United States Patent [19]

Guzzi et al.

[11] Patent Number: 5,254,595
[45] Date of Patent: Oct. 19, 1993

[54] ARYLOXYPROPANOLAMINOTETRALINS, A PROCESS FOR THEIR PREPARATION AND PHARMACEUTICAL COMPOSITIONS CONTAINING THEM

[75] Inventors: Umberto Guzzi, Milan; Marco Baroni, Vanzago; Sergio Boveri, Tortona; Luciano Manara, Pietra Marazzi; Alberto Bianchetti, Milan, all of

[73] Assignee: Elf Sanofi, Paris, France

[21] Appl. No.: 818,513

[22] Filed: Jan. 9, 1992

Related U.S. Application Data

[63] Continuation of Ser. No. 454,856, Dec. 22, 1989, abandoned.

[30] Foreign Application Priority Data

Dec. 23, 1988 [FR] France ................. 88 17139

[51] Int. Cl.$^5$ ................. C07C 237/02; C07C 215/56; A61K 31/165; A61K 31/135
[52] U.S. Cl. ................. 514/652; 514/226.2; 514/236.8; 514/241; 514/255; 514/311; 514/312; 514/351; 514/361; 514/373; 514/379; 514/381; 514/394; 514/396; 514/407; 514/411; 514/415; 514/418; 514/434; 514/443; 514/445; 514/454; 514/456; 514/457; 514/466; 514/469; 514/470; 514/479; 514/510; 514/561; 514/597; 514/630; 544/51; 544/134; 546/81; 546/176; 546/334; 548/136; 548/209; 548/241; 548/366.7; 548/251; 548/323.5; 548/343.1; 548/326; 548/370.1; 548/306.04; 548/343.5; 548/418; 548/484; 548/362.5; 548/361.1; 548/304.4; 549/40; 549/23; 549/51; 549/65; 549/391; 549/285; 549/366; 549/387; 549/466; 549/469; 549/479; 549/289; 558/422; 560/45; 560/139; 562/452; 564/51; 564/220; 564/349

[58] Field of Search ............. 564/349, 220, 51; 514/652, 630, 510, 561, 597; 558/422; 562/452; 560/45, 139

[56] References Cited

U.S. PATENT DOCUMENTS

| | | | |
|---|---|---|---|
| 3,466,325 | 9/1969 | Brandstrom et al. | 564/349 |
| 4,016,202 | 4/1977 | Köppe et al. | 564/349 |
| 4,853,383 | 8/1989 | Baldwin et al. | 514/235.8 |
| 4,952,730 | 8/1990 | Leuchs et al. | 564/349 |

FOREIGN PATENT DOCUMENTS

| | | |
|---|---|---|
| 2357849 | 6/1974 | Fed. Rep. of Germany . |
| 2401374 | 7/1974 | Fed. Rep. of Germany . |
| 2805404 | 8/1979 | Fed. Rep. of Germany . |
| 1184826 | 3/1970 | United Kingdom . |

Primary Examiner—Richard L. Raymond
Assistant Examiner—Peter G. O'Sullivan
Attorney, Agent, or Firm—Bacon & Thomas

[57] ABSTRACT

Aryloxypropanolaminotetralins with beta-antagonist activity of the formula

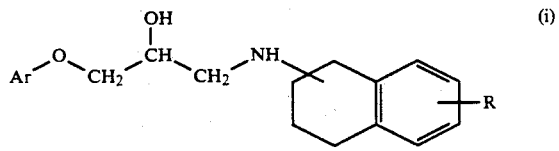

wherein R is hydrogen, hydroxy or methoxy and Ar is an optionally substituted aromatic or heteroaromatic group, in optically active or inactive form as well as their acid addition salts are described.

A process for their preparation and pharmaceutical compositions containing the compounds of formula (i) or their pharmaceutically acceptable acid addition salts, are also described.

11 Claims, No Drawings

ARYLOXYPROPANOLAMINOTETRALINS, A PROCESS FOR THEIR PREPARATION AND PHARMACEUTICAL COMPOSITIONS CONTAINING THEM

This application is a continuation of application Ser. No. 07/454,856, filed Dec. 22, 1989, now abandoned.

The present invention relates to beta-antagonists aryloxypropanolaminotetralins and salts thereof, a process for their preparation and pharmaceutical compositions containing said aryloxypropanolaminotetralins or their pharmaceutically acceptable salts, as the active principles.

It is known that beta-receptors are ubiquitous in the organism and that blockade of said receptors may affect several organs and metabolic systems.

The known beta-antagonists which inhibit the action of catecholamines on the beta-receptors of the cardiovascular tissue, have been put into medical use for the treatment of cardiovascular diseases, mainly as antihypertensive or antiarhythmic drugs.

Beta-receptors are however present also in the trachea as well as in the bronchi and therefore beta-antagonists may elicit a constriction of the above airways. For this reason research efforts have been directed to the development of cardioselective beta-antagonists devoid of respiratory side-effects.

Beta-adrenergic receptor antagonists have been proposed also for the treatment of diseases other than the cardiac ones, such as thyrotoxicosis, hyperparathyroidism, glaucoma, migraine and anxiety. In these cases not only any action on the trachea, but also on the heart represents an unwanted side-effect.

It is also known that beta-adrenergic receptors are present in the intestin and that both beta-agonists and beta-antagonists affect intestinal mothity.

Finally it is also known (EP-B-0211721 and EP-A-0255415) that some phenylethanolaminotetralins have an intestinal, selective, beta-agonist activity which does not affect the heart or the trachea.

It has now been found that by replacing the alkyl or aralkyl substituent of the amino group in the conventional beta-receptor antagonist aryloxypropanolamines with a tetralin, either a tetralin-1-yl or a tetralin-2-yl group, new compounds are obtained which, while retaining a beta-antagonist activity have a reduced activity on the heart.

It has been found that, with respect to the parent beta-blocker aryloxypropanolamines, the thus obtained aryloxypropanolaminotetralins have a higher beta-antagonist activity on the gastro-intestinal tract and a reduced activity or no activity at all on the heart and the trachea.

Accordingly, the primary aspect of this invention is the class of aryloxypropanolaminotetralins represented by the general formula:

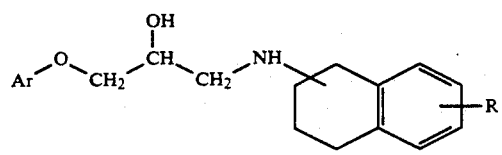

wherein R represents hydrogen, hydroxy or methoxy, and Ar represents an optionally substituted aromatic or heteroaromatic group, and their salts with mineral or organic acids (salts which are pharmaceutically acceptable or not).

In particular, in formula (i) above, Ar is an optionally susbtituted mono- , di- or tri-cyclic aromatic or heteroaromatic group wherein a carbon atom of the aromatic carbocyclic or heterocyclic moiety is directly linked to the oxygen atom.

More particularly, in formula (i) Ar represents the aromatic or heteroaromatic groups of the beta-antagonist aryloxypropanolamine compounds. Typically, Ar is the etherifying residue of the 3-positioned hydroxy group of a N-substituted 1-amino-2,3-propandiol, wherein said N-substituted 1-amino-2,3-propanediol ether has a beta-blocking adrenergic activity.

Mono-, di- and tri-cyclic aromatic groups include such radicals as optionally substituted phenyl, naphthyl, 5,6-, 5,8- and 7,8-dihydronaphthyl, 5,6,7,8-tetrahydronaphthyl, 5,8-ethano-5,6,7,8-tetrahydronaphthyl, 5,8-methano-5,6,7,8-tetrahydronaphthyl, 9,10-dihydro-9,10-ethano(or etheno)anthryl and fluorenyl.

Mono-, di- and tri-cyclic heteroaromatic groups include such radicals as phenyl fused to a 5 or 6- membered heterocycle containing 1, 2 or 3 heteroatoms independently selected from the group consisting of oxygen, nitrogen, and sulfur, said heterocycle in its turn being optionally fused to another benzene ring; phenyl fused to both a furan and a pyran ring; phenyl fused to the pyrrole moiety of a tetrahydropyrido(3,4-c)pyrrole group; 5- or 6-membered heterocyclic rings containing 1, 2, 3 or 4 heteroatoms selected from oxygen, nitrogen and sulfurs optionally fused to a benzene ring, said radicals and fused rings being optionally substituted.

More particularly, the radical Ar may represent a phenyl group, which may be unsubstituted or bear one or more substituents. As suitable substituents there may be cited: halogen, cyano, hydroxy, amino, formyl, nitro, carboxyl, carbamoyl, trifluoromethyl, alkyl, alkenyl, alkynyl, cycloalkyl, bicycloalkyl, alkanoyl, alkoxy, hydroxyalkyl, alkoxyalkyl, alkoxyalkoxyalkyl, alkoxyalkoxy, alkenyloxy, alkenyloxyalkyl, alkynyloxy, alkynyloxyalkyl, cycloalkoxy, alkylthio, alkylthioalkyl, morpholino, acylamino, acylaminoalkyl, acyloxy, alkoxycarbonyl, cycloalkoxycarbonyl, aminocarbonylamino, aminocarbonylaminoalkyl, dialkylaminocarbonylalkyl, dialkylaminocarbonylalkoxy, in the last two groups the terminal alkyls, together with the nitrogen atom, may also form a cyclic group containing 4 or 5 carbons, cycloalkylaminocarbonylamino, alkylaminocarbonylaminoalkyl, cycloalkylaminocarbonylaminoalkyl, alkoxycarbonylaminoalkyl, cycloalkoxycarbonylaminoalkyl, carbamoylalkyl, alkylaminocarbonylalkyl, cycloalkylaminocarbonylalkyl or alkylaminocarbonylalkoxy.

The radical Ar may also represent a group thiadiazolyl, naphthyl, indenyl, indolyl, indazolyl, imidazolyl, benzimidazolyl, benzotriazolyl, benzofuranyl, benzodioxolyl, benzothienyl, benzothiazolyl, benzisothiazolyl, quinolyl, isoquinolyl, benzodiazinyl, benzothiinyl, benzothiazinyl, benzothiadiazinyl, benzoxathiinyl, benzoxazolyl, benzisoxazolyl, benzoxazinyl, benzodioxinyl or carbazolyl wherein one or more double bonds may be hydrogenated, said groups unsubstituted or bearing one or more substituents such as: alkyl, cyano, hydroxyalkyl, hydroxy, oxo, formyl, alkanoyl, alkylcarbonylamino, alkoxycarbonyl and morpholino.

The phenyl group may preferably be mono- or disubstituted, mainly at the 2- and 5- positions, but also at the 2- and 3-, 2- and 4-, 3 and 4-, or 3- and 5- positions;

it may also be tri-substituted generally at positions 3-, 4-, and 5-, but also at positions 2-, 3-, and 4-, 2-, 3-, and 5- or 2-, 4-, and 5-; it may also be tetrasubstituted, for instance at positions 2-, 3-, 4-, and 5-; or pentasubstituted. The substituents of the phenyl group may be: F, Cl, Br, I, CN, OH, $NH_2$, NH—CO—$NH_2$, $NO_2$, COOH, $CONH_2$, $CF_3$, alkyl of from 1 to 10, preferably 1 to 4, carbon atoms, such as for instance n-propyl, isopropyl, n-butyl, isobutyl, sec-butyl, tert.-butyl, pentyl such as n-pentyl, hexyl such as n-hexyl, heptyl such as n-heptyl, octyl such as n-octyl, nonyl such as n-nonyl or decyl such as n-decyl, methyl and ethyl being preferred; alkenyl of from 2 to 10, preferably 2 to 4, carbon atoms, for instance vinyl, allyl, 1-propenyl, isopropenyl, butenyl i.e. 1-buten-1-, -2-, -3- or -4-yl, 2-buten-1-yl and 2-buten-2-yl, pentenyl, hexenyl or decenyl; alkynyl of from 2 to 10, preferably 2 to 4, carbon atoms, e.g. ethynyl, 1-propyn-1-yl, propargyl, butynyl or 2-butyn-1-yl, pentynyl, decynyl; cycloalkyl of from 3 to 8, preferably 5 or 6, carbon atoms, more preferably cyclopentyl or cyclohexyl, but also cyclopropyl, cyclobutyl, 1-, 2- or 3-methylcyclopentyl, 1-, 2-, 3- or 4-methylcyclohexyl, cycloheptyl or cyclooctyl; bicycloalkyl of from 4 to 11, preferably 7, carbon atoms, more preferably 2-norbornyl but also for instance 2-isobornyl or 5-camphyl; hydroxyalkyl of from 1 to 5, preferably 1 or 2, carbon atoms, more preferably hydroxymethyl and 1- or 2-hydroxyethyl but also, for instance, 1-hydroxyprop-1-yl, 2-hydroxyprop-1-yl, 3-hydroxyprop-1-yl, 1-hydroxyprop-2-yl, 1-hydroxybut-1-yl, 1-hydroxypent-1-yl; alkanoyl of from 1 to 7, preferably 1 to 4, carbon atoms, more preferably formyl, acetyl or propionyl but also, for instance butyryl, isobutyryl, valeroyl, caproyl, heptanoyl; alkoxy of from 1 to 10, preferably 1 to 4, carbon atoms, more preferably methoxy or ethoxy, but also, for instance, n-propoxy, isopropoxy, n-butoxy, isobutoxy, sec-butoxy, tert-butoxy, pentyloxy, hexyloxy, heptyloxy, octyloxy, nonyloxy or decyloxy; alkoxyalkyl of from 2 to 10, preferably 2 to 6, carbon atoms, such as for instance alkoxymethyl e.g. methoxymethyl, alkoxyethyl e.g. 1- or 2-methoxyethyl, 1- or 2-n-butoxyethyl, 1- or 2-n-octyloxyethyl; alkoxyalkoxyalkyl of up to 10, preferably from 4 to 7, carbon atoms, such as, for instance, alkoxyalkoxymethyl e.g. 2-methoxyethoxymethyl, 2-ethoxyethoxymethyl or 2-isopropoxyethoxymethyl, alkoxyalkoxyethyl e.g. 2-(2-methoxyethoxy)ethyl or 2-(2-ethoxyethoxy)ethyl; alkoxyalkoxy of from 2 to 10, preferably 3 to 6, carbon atoms, such as for instance 2-methoxyethoxy, 2-ethoxyethoxy or 2-n-butoxyethoxy; alkenyloxy of from 2 to 10, preferably 2 to 4, carbon atoms, more preferably allyloxy but also for instance vinyloxy, propenyloxy, isopropenyloxy, butenyloxy or 1-buten-1-, -2-, -3- or -4-yloxy, 2-buten-1-yloxy, 2-buten-2-yloxy, pentenyloxy, hexenyloxy or decenyloxy; alkenyloxyalkyl of up to 10, preferably from 3 to 6, carbon atoms, such as for instance allyloxymethyl; alkynyloxy of from 2 to 10, preferably 2 to 4, carbon atoms, more preferably propargyloxy, but also for instance ethynyloxy, 1-propyn-1-yloxy, butynyloxv or 2-butyn-1-yloxy, pentynyloxy or decynyloxv; alkynyloxyalkyl of from 3 to 10, preferably from 3 to 6 carbon atoms, e.g. ethynyloxymethyl, propargyloxymethyl or 2-(2-butyn-1-yloxy)ethyl; cycloalkoxy of from 3 to 8, preferably 5 or 6, carbon atoms, more preferably cyclopentyloxy or cyclohexyloxy but also for instance cyclopropyloxy, cyclobutyloxy, 1-, 2- or 3-methylcyclopentyloxy, 1-, 2-, 3- or 4-methylcyclohexyloxy, cycloheptyloxy or cyclooctyloxy; alkylthio of from 1 to 10, preferably 1 to 4, carbon atoms, more preferably methylthio or ethylthio, but also for instance n-propylthio, isopropylthio, n-butylthio, isobutylthio, sec-butylthio, tert-butylthio, pentylthio, hexylthio, octylthio, nonylthio and decylthio; alkylthioalkyl of from 1 to 10, preferably 2 to 6, carbons, e.g. methylthiomethyl, 2-methylthioethyl and 2-n-butylthioethyl; acylamino, more particularly alkanoylamino of from 1 to 7, preferably 1 to 4, carbon atoms, more preferably formylamino and acetylamino, but also propionylamino, butyrylamino, isobutyrylamino, valeroylamino, caproylamino, heptanoylamino, and aroylamino e.g. benzoylamino; acylaminoalkyl, preferably alkanoylaminoalkyl of from 2 to 8, preferably 3 to 6, carbon atoms, such as for instance formylaminoethyl, acetylaminoethyl, propionylaminoethyl, n-butyrylaminoethyl, formylaminopropyl, acetylaminopropyl, propionylaminopropyl, formylaminobutyl, acetylaminobutyl, propionylaminobutyl and butyrylaminobutyl; acyloxy of 1 to 6, preferably 2 to 4, carbon atoms, more preferably acetyloxy, propionyloxy and butyryloxy, but also formyloxy, valeroyloxy, caproyloxy; alkoxycarbonyl of from 2 to 5, preferably 2 and 3, carbon atoms, more preferably methoxycarbonyl and ethoxycarbonyl, but also n-propoxycarbonyl, isopropoxycarbonyl, n-butoxycarbonyl, isobutoxycarbonyl, sec-butoxycarbonyl and tert-butoxycarbonyl; cycloalkoxycarb,onyl of from 4 to 8, preferably 6 or 7, carbon atoms, more preferably cyclopentyloxycarbonyl, cyclohexyloxycarbonyl, but also cyclopropyloxycarbonyl, cyclobutyloxycarbonyl or cycloheptyloxycarbonyl; alkylaminocarbonylamino of from 2 to 4, carbon atoms, e.g. methylaminocarbonylamino, ethylaminocarbonylamino, propylaminocarbonylamino; dialkylaminocarbonylamino of from 3 to 7, preferably 3 to 5, carbon atoms, more preferably dimethylaminocarbonylamino, but also di-n-propylaminocarbonylamino, diisopropylaminocarbonylamino; (1-pyrrolidino)carbonylamino; (1-piperidino)carbonylamino; cycloalkylaminocarbonylamino of from 4 to 8, preferably 6 or 7, carbon atoms, more preferably cyclopentylaminocarbonylamino and cyclohexylaminocarbonylamino, but also cyclopropylaminocarbonylamino, cyclobutylaminocarbonylamino, cycloheptylaminocarbonylamino; alkylaminocarbonylaminoalkyl of from 3 to 9, preferably 4 to 7, carbon atoms, more preferably methylaminocarbonylaminoethyl, ethylaminocarbonylaminoethyl, ethylaminocarbonylaminopropyl and ethylaminocarbonylaminobutyl, but also for instance methylaminocarbonylaminomethyl, n-propylaminocarbonylaminobutyl, n-butylaminocarbonylaminobutyl; dialkylaminocarbonylaminoalkyl of from 4 to 11, carbon atoms, e.g. dimethylaminocarbonylaminomethyl, diethylaminocarbonylaminoethyl, diethylaminocarbonylaminopropyl, diethylaminocarbonylaminobutyl; (1-pirrolidino)carbonylaminoethyl; (1-piperidino)carbonylaminoethyl; cycloalkylaminocarbonylaminoalkyl of from 5 to 12, preferably 8 to 11, carbon atoms, more preferably cyclopentylaminocarbonylaminoethyl, cyclopentylaminocarbonylaminopropyl, cyclopentylaminocarbonylaminobutyl, cyclohexylaminocarbonylaminoethyl, cyclohexylaminocarbonylaminopropyl and cyclohexylaminocarbonylaminobutyl but also, for instance, cyclopropylaminocarbonylaminomethyl, cycloheptylaminocarbonylaminoethyl; alkoxycarbonylaminoalkyl of from 3 to 12, preferably 4 to 9, carbon atoms, more preferably methoxycarbonylaminoethyl, ethoxycarbonylaminoethyl, n-propoxycarbonylaminoethyl, isopropoxycarbonylaminoethyl, n-butoxycarbonylaminoethyl, isobutoxycarbonylaminoethyl, sec-butoxycarbonylaminoethyl, tert-butoxycarbonylaminoethyl, ethoxycarbonylaminopropyl, n-butoxycarbonylaminopropyl, ethoxycarbonylaminobutyl and n-butoxycarbonylaminobutyl but also, for instance, n-propoxycarbonylaminopropyl, n-propoxycarbonylaminobutyl, isopropoxycarbonylaminobutyl; cycloalkoxycarbonylaminoalkyl of from 5 to 12, preferably 8 to 11, carbons, more preferably cyclopentyloxycarbonylaminoethyl, cyclopentyloxycarbonylaminopropyl, cyclopentyloxycarbonylaminobutyl, cyclohexyloxycarbonylaminoethyl, cyclohexyloxycarbonylaminopropyl, cyclohexyloxycarbonylaminobutyl but also, for instance, cyclopropyloxycarbonylaminomethyl and cycloheptyloxycarbonylaminoethyl; carbamoylalkyl of from 2 to 5, preferably 2, carbon atoms, e.g. carbamoylmethyl, as well as carbamoylethyl, carbamoylpropyl and carbamoylbutyl; alkylaminocarbonylalkyl of from 3 to 9, preferably 3 to 6, carbon atoms, more preferably, methylaminocarbonylethyl, ethylaminocarbonylmethyl, n-propylaminocarbonylmethyl, isopropylaminocarbonylmethyl, n-butylaminocarbonylmethyl, isobutylaminocarbonylmethyl, sec-butylaminocarbonylmethyl and tertbutylaminocarbonylmethyl, but also, for instance ethylaminocarbonylethyl, ethylaminocarbonylpropyl, ethylaminocarbonylbutyl, n-propylaminocarbonylbutyl, n-butylaminocarbonylbutyl; dialkylaminocarbonylalkyl of from 4 to 11, preferably 4 to 8, carbon atoms, more preferably dimethylaminocarbonylmethyl, diethylaminocarbonylmethyl, di-n-propylaminocarbonylmethyl, (1-pirrolidino)carbonylmethyl and (1-piperidino)carbonylmethyl, but also, for instance, diethylaminocarbonylethyl, (1-piperidino)carbonylethyl, diethylaminocarbonylpropyl, diethylaminocarbonylbutyl; cycloalkylaminocarbonylalkyl of from 5 to 12, preferably 7 or 8, carbon atoms, more preferably, cyclopentylaminbcarbonylmethyl and cyclohexylaminocarbonylmethyl, but also, for instance cyclopropylaminocarbonylmethyl, cyclobutylaminocarbonylmethyl, cycloheptylaminocarbonylmethyl, cyclohexylaminocarbonylethyl, cyclohexylaminocarbonylpropyl, cyclohexylaminocarbonylbutyl; alkylaminocarbonylalkoxy of from 3 to 10, preferably 3 to 5, carbon atoms, more preferably, methylaminocarbonylmethoxy but also, for instance methylaminocarbonylethoxy and methylaminocarbonylpropoxy; dialkylaminocarbonylalkoxy of from 4 to 10, preferablv 4 to 7, carbon atoms, such as for instance dimethylaminocarbonylmethoxy, diethylaminocarbonvlethoxy and (1-piperidino)carbonylmethoxy; cycloalkylaminocarbonylalkoxy of from 5 to 11, preferably 7 or 8 carbon atoms, such as for instance cyclopentylaminocarbonylmethoxy and cyclohexylaminocarbonylmethoxy.

Ar may also represent, for instance, one of the following radicals: 1,2,5-thiadiazol-3-yl, 4-(N-morpholino)-1,2,5-thiadiazol-3-yl; 1- or 2-naphthyl; 1-, 2-, 3-, (preferably) 4-, 5-, 6- or 7-indanyl; 1-oxo-4-, -5-, -6-, or (preferably) -7-indanyl; alkyl-1-oxoindanyl, preferably 1-oxo-5-methyl-7-indanyl; 1-hydroxy-4-, -5-, -6- or (preferably) -7-indanyl; 1-, 2-, 3-, (preferably) 4-, 5-, 6- or 7-indenyl; 1-, 2-, 3-, 4-, (preferably) 5-, 6-, 7- or 8-tetralyl; oxo-tetralyl, preferably 1-oxo-5-tetralyl, as well as 2-, 3- or 4-oxo-5-tetralyl or 1-, 2-, 3- or 4-oxo-6-tetralyl; hydroxytetralyl, (preferably) 1-hydroxy-5-tetralyl, but also 2-, 3- or 4-hydroxy-5-tetralyl; (preferably) 4-, 5-, 6- or 7-indolyl; alkylindolyl, preferably methylindolyl, such as for instance 2-methyl-4-indolyl, 3-methyl-4-indolyl and 6-methyl-4-indolyl, but also, for instance 2-ethyl-4-indolyl and 6-ethyl-4-indolyl; dialkylindolyl, preferably dimethylindolyl, e.g. 2,3-dimethyl-4-indolyl, 2,6-dimethyl-4-indoly, but also, for instance, 2-methyl-3-ethyl-4-indolyl, 2-ethyl-3-methyl-4-indolyl, 2,3-diethyl-4-indolyi; cyanoindolyl, e.g. 2-cyano-4-indolyle, 3-cyano-4-indolyl; alkyl-cyano-indolyl, preferably 2-cyano-6-methyl-4-indolyl, but also for instance 3-cyano-6-methyl-4-indolyl; carbamoylindolyl, preferably 2-carbamoyl-4-indolyl, 4-carbamoyl-4-indolyl, but also, for instance 6-carbamoyl-4-indolyl; alkyl-carbamoyl-indolyl, preferably methylcarbamoyl-indolyl, e.g. 2-carbamoyl-6-methyl-4-indolyl; hydroxyalkylindolyl, preferably 2-hydroxymethyl-4-indolyl, but also, for instance 2-hydroxymethyl-5-indolyl, 3-hydroxymethyl-4-indolyl, 2-(2-hydroxyethyl)-4-indolyl; 2-oxo-indolinyl, preferably 2-oxo-indolin-4-yl, but also 2-oxo-indolin-5-yl; alkyl-2-oxo-indolinyl, preferably methyl-2-oxo-indolin-4-yl, e.g. 3-methyl-2-oxo-indolin-4-yl, but also, for example 3-ethyl-2-oxo-indolin-4-yl, 3-isopropyl-2-oxo-indolin-4-yl; dialkyl-2-oxo-indolinyl, e.g. 3,3-dimethyl-2-oxo-indolin-4-yl and 3,3,-diethyl-2-oxo-indolin-4-yl; indazol- (preferably) -4-, -5-, -6-or 7-yl; benzimidazol-4-yl; alkyl-benzimidazol-4-yl, preferably methyl-benzimidazol-4-yl, e.g. 3-methyl-benzimidazol-4-yl, 1-methyl-benzimidazol-4-yl, 2-methyl-benzimidazol-4-yl, 6-methyl-benzimidazol-4-yl and 7-methyl-benzimidazol-4-yl; benzimidazolin-2-on-4-yl (preferably), benzimidazolin-2-on-5-yl; alkylbenzimidazolin-2-on-4-yl, preferably, methyl-benzimidazolin-2-on-4-yl, e.g. 6-methyl-benzimidazolin-2-on-4-yl, 7-methyl-benzimidazolin-2-on-4-yl; benzotriazol- (preferably) 4- or 5-yl; benzofuran- (preferably) 4-, 5-, 6- or 7-yl; alkylbenzofuran-4-yl, e.g. 2-methylbenzofuran-4-yl, 3-methylbenzofuran-4-yl, and 6-methylbenzofuran-4-yl; alkanoylbenzofuran-4-yl, e.g. 2-acetylbenzofuran-4-yl and 6-acetylbenzofuran-4-yl; bis-alkanoyl-benzofuranyl, e.g. 2,4-diacetylbenzofuran-5-yl, and 2,6-diacetylbenzofuran-4-yl; 1,3-benzodioxolyl, preferably 1,3-benzodioxol-4-yl; alkyl-1,3-benzodioxolyl, preferably 2-methyl-1,3-benzodioxol-4-yl, but also, for instance 6-methyl-1,3-benzodioxol-4-yl; dialkyl-1,3-benzodioxolyl, preferably 2,2-dimethyl-1,3-benzodioxol-4-yl, but also, for instance 2,2-diethyl-1,3-benzodioxol-4-yl, and 2,6-dimethyl-1,3-benzodioxol-4-yl; 1,2-benzisoxazol- (preferably) 4- 5-, 6- ou 7-yl; alkyl-1,2-benzisoxazolyl, preferably 3-methyl-1,2-benzisoxazol- 4-yl, but also, as an example 3-ethyl-1,2-benzisoxazol-4-yl, 3-propyl-1,2-benzisoxazol-4-yl, 3-isopropyl-1,2-benzisoxazol-4-yl, and 6-methyl-1,2-benzisoxazol-4-yl; 1,3-benzoxazol-(preferably) 4-, 5-, 6- or 7-yl; alkyl-1,3-benzoxazolyl, preferably 2-methyl-1,3-benzoxazol-4-yl, but also, for instancee 2-e hyl-1,3-benzoxazol;-4-yl, 6-methyl-1,3-benzoxazol-4-yl, and 6-ethyl-1,3-benzoxazol-4-yl; aryl-1,3-benzoxazolyl, preferably 2-phenyl-1,3-benzoxazol-4-yl, and 2-(4-pyridyl)-1,3-benzoxazol-4-yl; benzothien- (preferably) 4-, 5-, 6- or 7-yl; 1,2-benzisothiazol- (preferably) 4-, 5-, 6- or 7-yl; alkyl-1,2-benzisothiazolyl, e.g. 6-methyl-1,2-benzisothiazol-4-yl; 1,3-benzothiazol-4-5-, -6- or (preferably) -7-yl; 1,3-benzothiazol-7-yl, e.g. 2-methyl-1,3-benzothiazol-7-yl, 4-methyl-1,3-benzothiazol-7-yl, and 2-ethyl-1,3-benzothiazol-7-yl; 2-aryl-1,3-benzothiazol-7-yl, e.g. 2-phenyl-1,3-benzothiazol-7-yl and 2-(4-chlorophenyl)-1,3-benzothiazol-7-yl; 2-(4-pyridyl)-1,2-benzothiazol-7-yl; 1,2-dihydro-2-oxo-3-, -4-, (preferably) -5-, -6-, -7- or -8-quinolinyl; 1,2,3,4-tetrahydro-(preferably) -5-, -6-, -7- or -8-quinolinyl; 1,2,3,4-tetrahydro-2-oxo (preferably) -5-, -6-, -7- or -8-quinolinyl; 1,2-dihydro-8-hydroxy-2-oxo- (preferably) -5-, -6- or -7-quinolinyl; 1,2-dihydro-8-alkoxy-2-oxo- (preferably) -5-, -6- or -7-quinolinyl, e.g. 1,2-dihydro-8-methoxy-2-oxo-5-quinolinyl; 1,2,3,4-tetrahydro-8-hydroxy-2-oxo- (preferably) -5-, -6-, or -7-quinolinyl; 1,2,3,4-tetrahydro-8-alkoxy-2-oxo- (preferably) -5-, -6- or -7-quinolinyl, e.g. 1,2,3,4-tetrahydro-8-methoxy-2-oxo-5-quinolinyl; 1,2,3,4-tetrahydro-8-alkanoylamino-2-oxo- (preferably) -5-, -6- or -7-quinolinyl, e.g 1,2,3,4-tetrahydro-8-acetylamino-2-oxo-5-quinolinyl; 1,2-dihydro-3-cyano-2-oxo- (preferably) -5-, -6-, -7- or -8-quinolinyl; 1,2-dihydro-3-cyano-2-oxo-7-methyl-5-quinolinyl; 1,2-dihydro-1-oxo- (preferably) -4-, -5-, -6-, -7- or -8-isoquinolinyl; 1,2-dihydro-2-alkyl-1-oxo- (preferably) -4-, -5-, -6-, -7- or -8-isoquinolinyl, e.g. 1,2-dihydro-2-methyl-1-oxo-4-isoquinolinyl; 1,2,3,4-tetrahydro-2-alkanoyl- (preferably) -5-, -6-, -7- or -8-isoquinolinyl, such as 1,2,3,4-tetrahydro-2-formyl-5-isoquinolinyl, or 1,2,3,4-tetrahydro-2-acetyl-5-isoquinolinyl; 1,2-dihydro-2-oxo-1,3-benzodiazin- (preferably) -5-, -6-, -7- or -8-yl; 2H-3,4-dihydro-5-, -6-, -7- or (preferably) -8-benzopyranyl; 2H-5-, -6-, -7- or (preferably) -8-benzopyranyl; 2H-2-oxo-5-alkyl-7- or (preferably) -8-benzopyranyl, for instance 2H-2-oxo-5-methyl-8-benzopyranyl; 2H-3-cyano-5-, -6-, -7- or (preferably) 8-benzopyranyl; 2H-3,4-dihydro-5-, -6-, -7- or (preferably) -8-benzothiinyl; 3,4-dihydro-1H-2,2-dioxo-2,1-benzothiazin- (preferably) 5-, 6-, 7- or 8-yl; 3,4-dihydro-1H-1-alkyl-2,2-dioxo-2,1-benzothiazin- (preferably) 5-, 6-, 7- or 8-yl, e.g. 3,4-dihydro-1H-1-methyl-2,2-dioxo-2,1-benzothiazin-5-yl; 3,4-dihydro-2H-3-oxo-1,4-benzothiazin-5-, -6-, -7- or (preferably) -8-yl; 5- or 6-alkyl-3,4-dihydro-3-oxo-1,4-benzothiazin-8-yl, e.g. 6-methyl-3,4-dihydro-3-oxo-1,4-benzothiazin-8-yl; 1,1-dioxo-1,2,4-benzothiadiazin-5-, -6-, -7- or -8-yl; 1,1-dioxo-3-alkyl-1,2,4-benzothiadiazin-5-, -6-, -7- or -8-yl, e.g. 1,1-dioxo-3-methyl-1,2,4-benzothiadiazin-5-, -6-, -7- or -8-yl; 1,1-dioxo-3-alkanoyl-1,2,4-benzothiadiazin-5-, -6-, -7- or -8-yl, e.g. 1,1-dioxo-3-formyl-1,2,4-benzothiadiazin-5-, -6-, -7- or -8-yl, 1,1-dioxo-3-acetyl-1,2,4-benzothiadiazin-5-, -6-, -7- or -8-yl; 1,1-dioxo-3-aroyl-1,2,4-benzothiadiazin-5-, -6-, -7- or -8-yl, e.g. 1,1-dioxo-3-benzoyl-1,2,4-benzothiadiazin-5-, -6-, -7- or -8-yl; 1,1-dioxo-3-(4-pyridyl-carbonyl)-1,2,4-benzothiadiazin-5-, -6-, -7- or -8-yl; 3,4-dihydro-2,2-dioxo-1,2-benzoxathiin- (preferably) -5-, -6-, -7- or (preferably) -8-yl; 1-, 2-, 3- or (preferably) 4-carbazolyl.

In particular, when in formula (i), Ar is an aromatic or heteroaromatic group as defined hereinabove, said aromatic or heteroaromatic group may be represented by one of following structures 1 to 67.

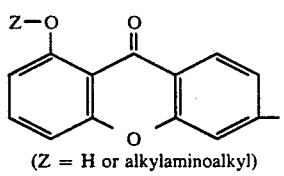

1

(Z = H or alkylaminoalkyl)

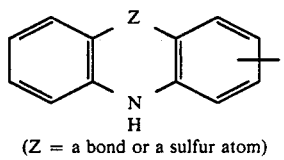

2

(Z = a bond or a sulfur atom)

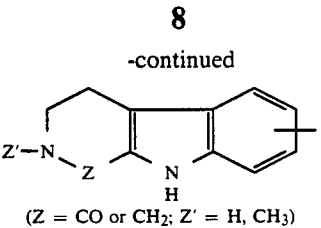

3

(Z = CO or CH$_2$; Z' = H, CH$_3$)

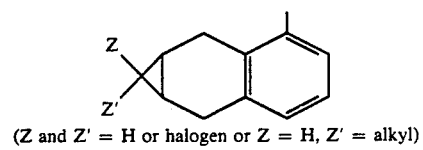

4

(Z and Z' = H or halogen or Z = H, Z' = alkyl)

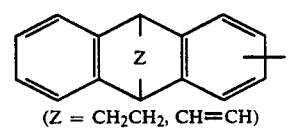

5

(Z = CH$_2$CH$_2$, CH=CH)

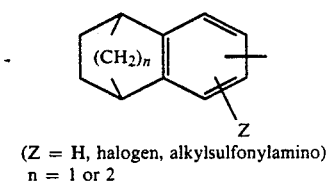

6

(Z = H, halogen, alkylsulfonylamino)
n = 1 or 2

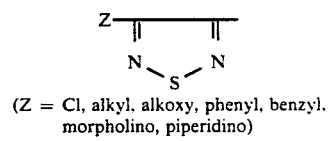

7

(Z = Cl, alkyl, alkoxy, phenyl, benzyl, morpholino, piperidino)

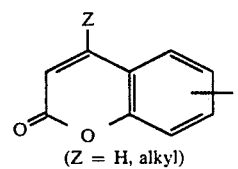

8

(Z = H, alkyl)

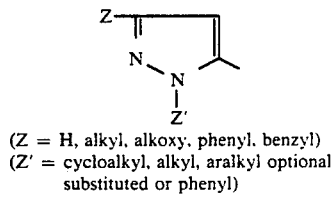

9

(Z = H, alkyl, alkoxy, phenyl, benzyl)
(Z' = cycloalkyl, alkyl, aralkyl optional substituted or phenyl)

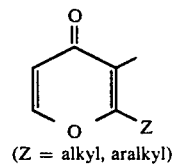

10

(Z = alkyl, aralkyl)

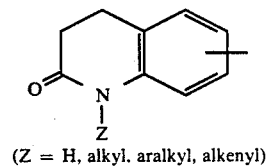

11

(Z = H, alkyl, aralkyl, alkenyl)

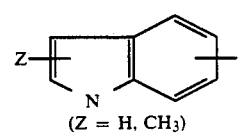

12

(Z = H, CH$_3$)

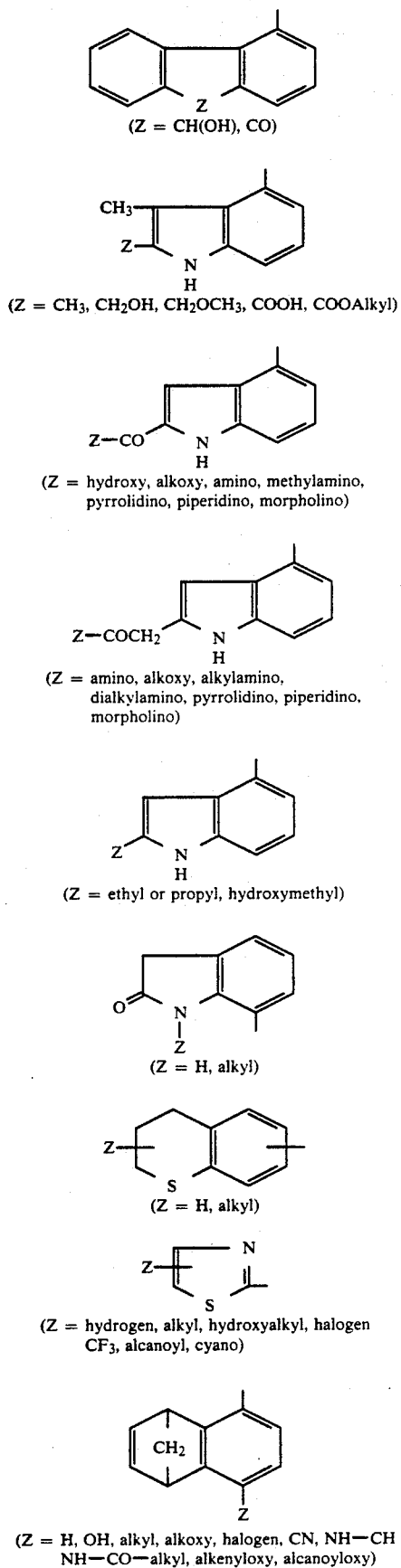
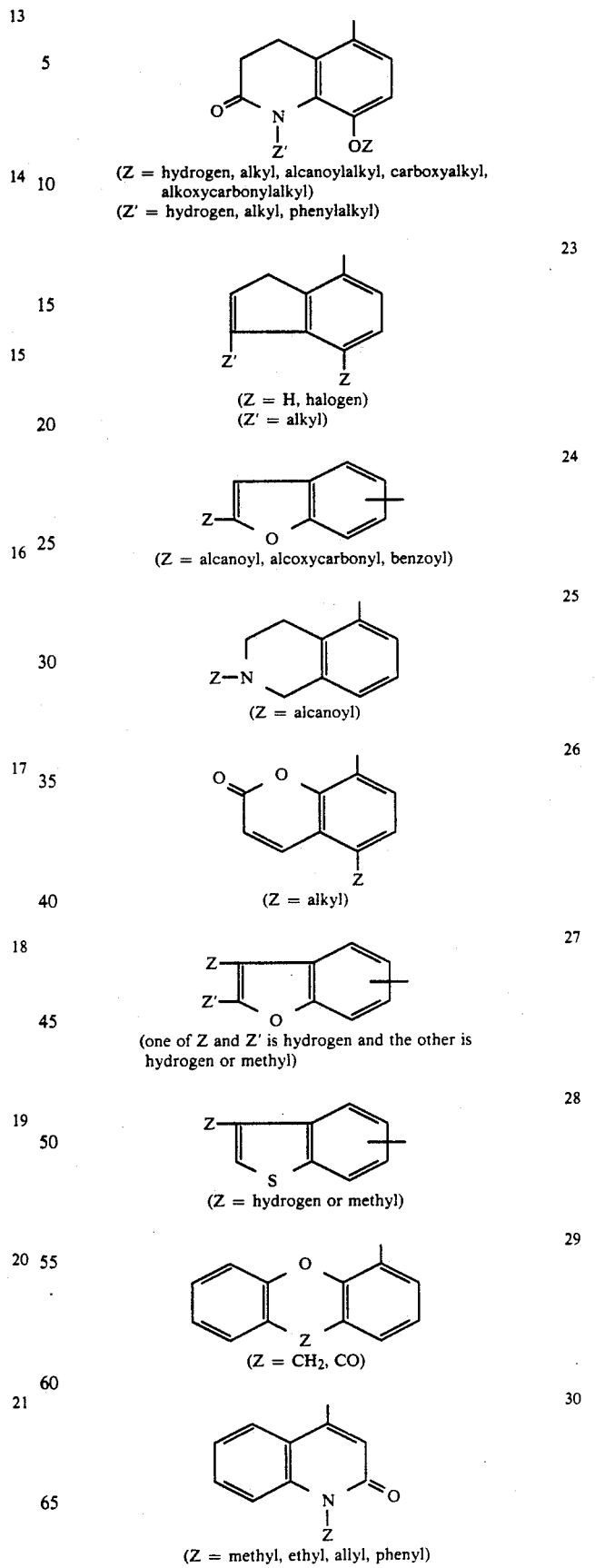

-continued
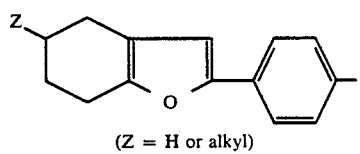
(Z = H or alkyl)
31
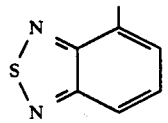
32
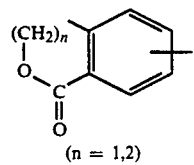
(n = 1,2)
33
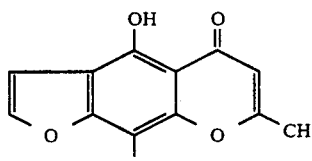
34
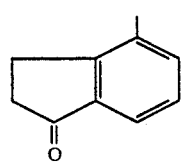
35
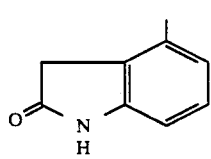
36
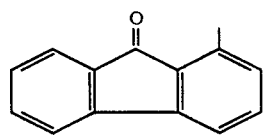
37
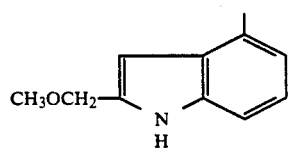
38
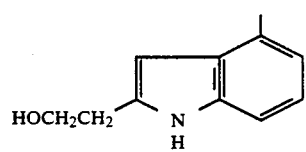
39
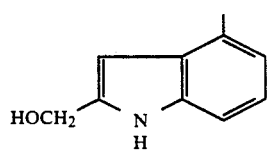
40
-continued
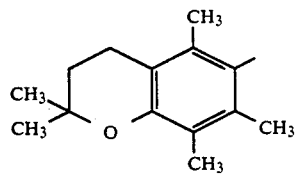
41
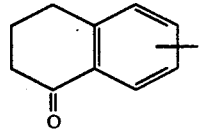
42
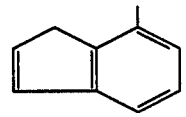
43
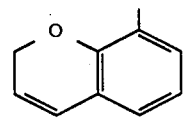
44
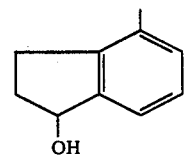
45
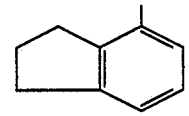
46
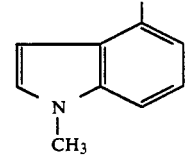
47
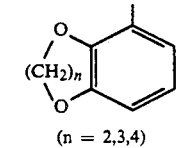
(n = 2,3,4)
48
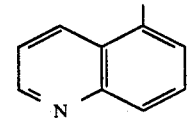
49
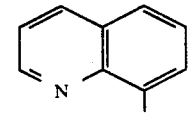
50

-continued

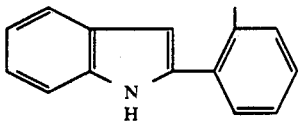 51

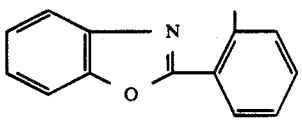 52

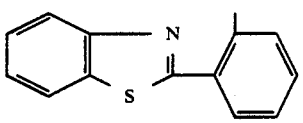 53

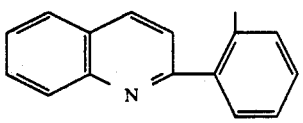 54

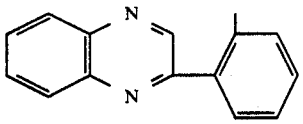 55

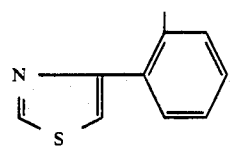 56

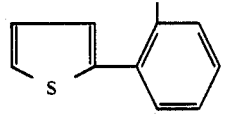 57

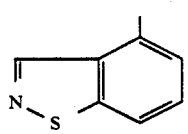 58

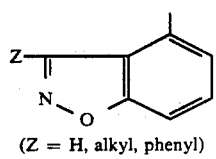 59
(Z = H, alkyl, phenyl)

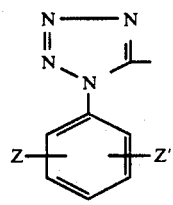
(Z = H, halogen, $NO_2$, acetamido)
(Z' = H, $CH_3$)

-continued

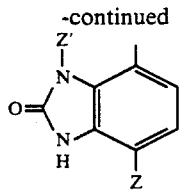 61
(Z and Z' = H, $CH_3$)

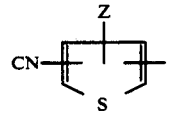 62
(Z = H, alkyl, phenylalkyl, phenyl unsubstituted or substituted with halogen, alkyl, alkoxy, alkylthyl, $CF_3$, OH, carboxy, methylenedioxy)

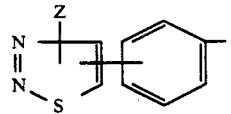 63
(Z = alkyl, H, phenyl, CN, $CF_3$, COOH, COOAlkyl, aminocarbonyl, alkylaminocarbonyl, dialkylaminocarbonyl)

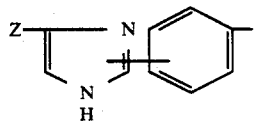 64
(Z = H, alkyl, phenyl, $CF_3$)

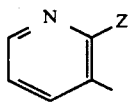 65
(Z = H, $NH_2$)

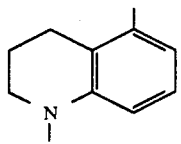 66
(Z = H, alkyl)

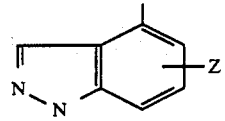 67
(Z = H, alkyl, Z' = H, acetyl)

According to a preferred embodiment, the present invention relates to those compounds of formula (i) above, wherein R is as defined above and Ar represents
(a) a phenyl group, which may be unsubstituted or bear one or more substituents, optionally fused, at positions 2 and 3, to a 5- or 6-membered carbocycle which
may contain one or two double bonds,
may bear one or two substituents,
may be fused to a benzene ring, or when said carbocycle is a 6-membered ring, may bear a methano or ethano bridge connecting positions 3 and 6;

(b) a phenyl ring fused, at positions 3 and 4, to a 5-membered heterocycle containing both a nitrogen atom and a sulfur atom or an —NH— group, or an optionally substituted phenyl ring fused at positions 2 and 3 to a 5- or 6-membered, aromatic or non-aromatic, heterocycle which contains a nitrogen, oxygen or sulfur atom or an —NH— or —NAlkanoyl- group, and may contain a double bond or bear a substituent such as a lower alkyl, in particular methyl, an alkanoyl, typically acetyl, or an oxo group;

a 5-membered heteroaromatic group containing both a nitrogen atom and a sulfur atom or an —NH— group;

a 6-, 7- or 8-membered heterocycle, saturated in the non fused portion, containing two oxygen atoms directly linked to the phenyl group;

(c) a phenyl group, optionally substituted at position 4-, fused, at positions 2 and 3, and 5 and 6 to an (a)-furan and a (b)-4-oxopyran;

(d) a 4-carbazolyl;

(e) an optionally substituted 2-thiazolyl;

(f) an optionally 4-substituted 3-(1,2,5)-thiadiazolyl; and their salts with mineral or organic acids.

In meaning (a) above, as suitable substituents of the phenyl ring there may be cited, as an example, one or more halogen atoms, e.g. fluoro, chloro, bromo or iodo atoms, alkyl, alkoxy or alkylthio radicals, e.g. methyl, ethyl, isopropyl, t-butyl, methoxy, ethoxy, n-butoxy or methylthio, acyl radicals, e.g. acetyl, phenylalkanoyl or benzoyl, the hydroxy group, haloalkyl radicals, preferably trifluoromethyl, phenyl, phenoxy, 4-tolyloxy, phenylthio, phenylsulfonyl, anilino, morpholino, benzyl, alpha,alphadimethylbenzyl, benzyloxy, the nitro group, alkenyl radicals and the cyano group.

More particularly, when in meaning (a) above, Ar is a phenyl group bearing only one substituent at position 2, preferably said substituent is alkyl or alkeng, optionally halo substituted, alkynyl, optionally substituted alkoxy, alkylthio, alkenyloxy, alkynyloxy, tetrahydrofurfuryloxy, phenoxy, halogen, cyano, cycloalkyl, cycloalkenyl, 2,5-methanocyclohexyl, alkanoyl, phenylalkanoyl, benzoyl, 2-indolyl, 2-benzoxazolyl, 2-benzothiazolyl, 2-quinolinyl, 2-quinoxalinyl, 2-thienyl, 4-thiazolyl, 4-morpholinyl.

When in meaning (a) above, Ar is a phenyl group bearing only one substituent at the 3-position, said substituent is preferably a halogen atom, an optionally halo-substituted alkyl group, in particular trifluoromethyl, an alkenyl group, in particular an allyl group, or a cyano group.

When in meaning (a) above, Ar is a phenyl group bearing only one substituent at the 4-position, said substituent is preferably an alkyl group optionally substituted with one or more halogen atoms, alkoxy, alkoxycarbonylamino, carbamoyl or cycloalkylalkoxy, an alkenyl group optionally substituted with halogen or cyano, or an acylamido, haloacylamido or 3-cycloalkylureido group.

When in meaning (a), Ar represents a phenyl group bearing two substituents, said substitutents may be two halogen atoms, two alkyl groups, a halogen atom and an alkyl group, or one is a 2-acyl group, e.g. acetyl or benzoyl, and the other is halogen, acylamido, e.g. acetylamino, butyrylamino, or benzoylamino, or 3- mono- or di-substituted ureido or one is a hydroxy group and the other is alkyl, hydroxymethyl, nitro or carbamoyl, or one is alkyl and the other is alkylthio, or one is a 2-acetamido or 4-acetamido group and the other is a 3-nitro group.

The phenyl group in meaning (a) may also contain 3, 4 or 5 substituents.

Additionally as suitable substituents of the phenyl group (a) there may be mentioned: 2-methyl, 3-methyl, 4-methyl, 4-isopropyl, 2,3-dimethyl, 2,4-dimethyl, 2,5-dimethyl, 3,4-dimethyl, 3,5-dimethyl, 3-methyl-5-ethyl, 2-t-butyl-5-methyl, 2-allyl, 2-chloro, 3-chloro, 4-chloro, 2,3-dichloro, 2,5-dichloro, 3,4-dichloro, 3,5-dichloro, 2,4,5-trichloro, 2-iodo, 3-bromo, 3-fluoro, 4-chloro-3-methyl, 2-chloro-4-methyl, 4-chloro-3,5-dimethyl, 2,4,6-tribromo-3,5-dimethyl, 2-methoxy, 3-methoxy, 2-allyloxy, 2-propargyloxy, 3,5-dimethoxy, 2,3-dimethoxy, 3-t-butyl-4-methoxy, 3-ethoxy, 2-hydroxy, 4-hydroxy, 2-nitro, 3-nitro, 2-acetamido-3-nitro, 4-acetamido-3-nitro, 3-trifluoromethyl, 4-acetyl, 2-phenyl, 2-phenoxy, 3-phenoxy, 3-(4-tolyloxy), 2-benzyl, 2-benzoyl-5-methoxy, 2-phenylthio, 2-cyano, 3-cyano, 4-cyano.

When in meaning (a) above, the phenyl group is fused to a 5- or 6-membered carbocycle, preferably Ar represents one of the following radicals: 4-indenyl, 4-indanyl, 1-naphthyl, 5,6-dihydro-1-naphthyl, 5,6,7,8-tetrahydro-1-naphthyl, 5,8-dihydro-1-naphthyl, 6,7-dihydroxy-5,6,7,8-tetrahydro-1-naphthyl, 5,8-ethano-5,6,7,8-tetrahydro-1-naphthyl, optionally substituted at position 4 with hydroxy, acylamido or alkylsulfonylamino, 5-oxo-5,6,7,8-tetrahydronaphthyl, 8-oxo-5,6,7,8-tetrahydronaphthyl, or 9-oxo-4-fluorenyl.

A preferred group of compounds of formula (i) wherein Ar has meaning (a) above, comprises those aryloxypropanolaminotetralins which can be better represented by following formula (iA)

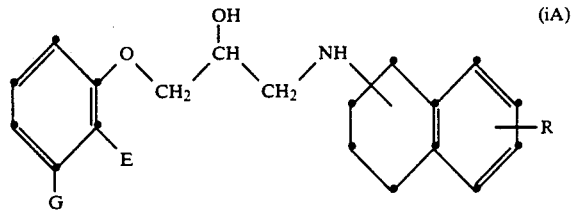

wherein R is as defined above, E represents hydrogen, halogen, alkyl, alkenyl, alkynyl, alkoxy, alkenyloxy, alkynyloxy, tetrahydrofurfuryloxy, phenoxy, ($C_{3-C6}$-)cycloalkyl, 1-cyclohexenyl, 2-cyclohexenyl, 2,5-methanocyclohexyl, alkylthio, alkanoyl, phenylalkanoyl, cyano, 3-chloroallyl, 2-indolyl, 2-benzoxazolyl, 2-benzothiazolyl, 2-quinolinyl, 2-quinoxalyl, 2-thienyl, 4-thiazolyl or 4-morpholinyl, G is hydrogen, halogen, alkyl, alkenyl, trifluoromethyl, cyano or acetamido, wherein at least one of E and G is hydrogen, or E and G represent, respectively, an acetamido and a nitro group or E and G taken together represent a group —CH$_2$—CH$_2$—CH$_2$—, —CH$_2$—CH$_2$—CH$_2$—CH$_2$—, —CH=CH—CH$_2$—, —CH$_2$—CH=CH—, —CH=CH—CH$_2$—CH$_2$—, —CH=CH—CH=CH—, —CO—CH$_2$—CH$_2$—CH$_2$—, —CH$_2$—CH$_2$—CH$_2$—CO— or —CH$_2$—CH(OH)—CH(OH)—CH$_2$—, and their salts with mineral or organic acids.

Among the compounds of formula (iA) a particularly preferred subclass comprises those compounds wherein R is as defined above, E represents hydrogen, halogen, alkyl, alkenyl, alkynyl, alkoxy, alkenyloxy or alkynyloxy, G is hydrogen or E and G taken together represent a group —CH₂—CH₂—CH₂—, —CH₂—CH₂—CH₂—CH₂—, —CH=CH—CH₂—, —CH₂—CH=CH—, —CH=CH—CH₂—CH₂—, —CH=CH—CH=CH—, —CO—CH₂—CH₂—CH₂—, —CH₂—CH₂—CH₂—CO— or —CH₂—CH(OH)—CH(OH)—CH₂—, and their salts with mineral or organic acids.

An even more preferred subclass comprises those compounds of formula (iA) wherein R is as defined above, E represents a halogen atom, an alkyl, alkenyl, alkoxy, alkenyloxy, or alkynyloxy group and G is hydrogen or E and G taken together represent a group —CH=CH—CH=CH— or —CH₂—CH(OH)—CH(OH)—CH₂—, and their salts with mineral or organic acids.

The compounds of formula (iA) wherein R is hydrogen or hydroxy, E is allyloxy and G is hydrogen, their optically active forms (SR), (SS), (RS) and (RR), and their salts are of particular interest.

Also the compound of formula (iA) wherein R is hydrogen, the amino group is linked to the 1-position of the tetralin moiety and E and G taken together form a —CH=CH—CH=CH— group, its optically active forms and the corresponding salts are particularly preferred.

Another preferred group of compounds of the present invention of above formula (i) wherein Ar has meaning (a), comprises those aryloxypropanolaminotetralins which can be represented by following formula (iB)

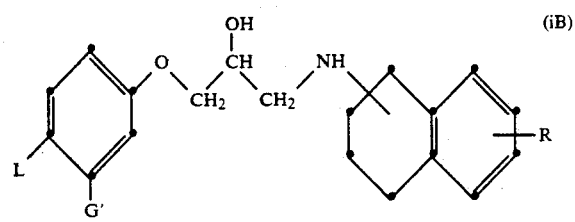

wherein R is as defined above, G' is hydrogen and L represents halogen; unsubstituted alkyl or alkyl substituted with alkoxy, alkoxycarbonylamino, aminocarbonyl, cycloalkylalkoxy; unsubstituted alkenyl or cyanosubstituted alkenyl; alkanoylamino or haloalkanoylamino; ureido N'-mono or di-substituted with alkyl or cycloalkyl; alkoxy optionally substituted with alkoxy; cyano; or a hydroxymethyl group etherified with an alkoxyalkyl group; or G' and L represent a nitro and an acetamido group respectively, and their salts with mineral or organic acids.

Among the compounds of formula (iB) a particularly preferred subclass comprises those compounds wherein R is as defined above, G' represents hydrogen and L is chloro, cyano or 2-methoxyethyl or G' and L taken together form a group —CH=CH—CH=H—.

Another preferred group Of compounds of the present invention of formula (i) above wherein Ar has meaning (a), comprises those aryloxypropanolaminotetralins which can better be represented by following formula (iC)

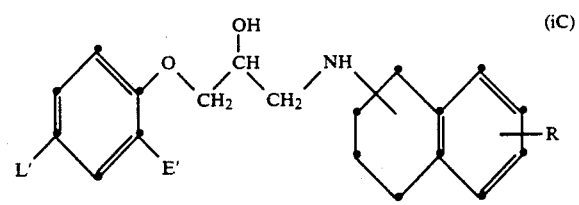

wherein R is as defined above, E' represents an alkanoyl group and L' represents halogen, alkanoylamino or ureido N'-mono or di-substituted with alkyl, and their salts with mineral or organic acids.

A further preferred group of compounds of the present invention of above formula (i), wherein Ar has meaning (a), comprises those aryloxypropanolaminotetralins which can be represented by formula (iD) below

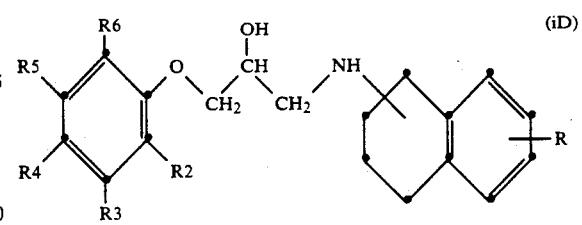

wherein R is as defined above and:
R2 to R6 are independently selected from hydrogen, halogen, alkoxy and alkylthio with the proviso that at least two of them are different from hydrogen; or
one of R4 and R5 represents hydroxy and the other is hydrogen, R3 represents a group —COHN₂ or —CH₂OH, R2 and R6 are hydrogen; or
R4 represents an alkanoyloxy group, R2, R3 and R5 are methyl and R6 is hydrogen;
and their salts with mineral or organic acids.

Another preferred group of compounds of formula (i), wherein Ar has meaning (a), comprises those aryloxypropanolaminotetralins which can better be represented by following formula (iE)

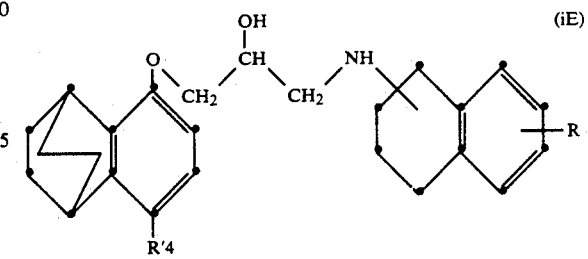

wherein R is as defined above and R'4 is hydrogen, hydroxy, alkanoyloxy or alkylsulfonylamino, and their salts with mineral or organic acids.

A preferred group of compounds of formula (i), wherein Ar has meaning (b) comprises those aryloxypropanolaminotetralins which can better be represented by following formula (iF)

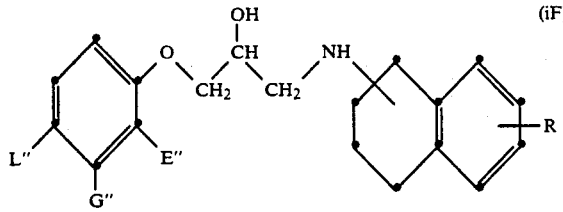
(iF)

wherein R is as defined above, and
E" is hydrogen and G" and L", taken together, represent a group —N=CH—NH— or —S—CH=N—; or L" is hydrogen and E" and G", taken together, represent a group —CH=CH—NH—; —CH=C(CH$_3$)—NH—, —CH=CH—O—, —C(CH$_3$)=CH—O—, —CH=C(CH$_3$)—O—, —CH=C(COCH$_3$)—O—, —CO—O—CH$_2$, —N=CH—NH—, —S—CH$_2$CH$_2$—CH$_2$—, —O—CH$_2$CH$_2$— or —CH$_2$—CH$_2$—N(CHO)—CH$_2$—; or
L" is hydrogen, methyl or acetonyloxy and E" and G", taken together, represent a group —CH$_2$—CH$_2$—CO—NH—; or
L" is hydrogen or methyl and E" and G", taken together, represent a group —O—CO—CH=CH—; and their salts with mineral or organic acids.

Among the compounds of formula (iF), a particularly preferred subclass comprises those compounds wherein R is as defined above, L" is hydrogen and E" and G", taken together represent a group —CH=CH—NH—, and their salts with mineral or organic acids.

A preferred group of compounds of formula (i), wherein Ar has meaning (c), comprises those aryloxypropanolaminotetralins which can be represented by following formula (iG)

following formula (iG)

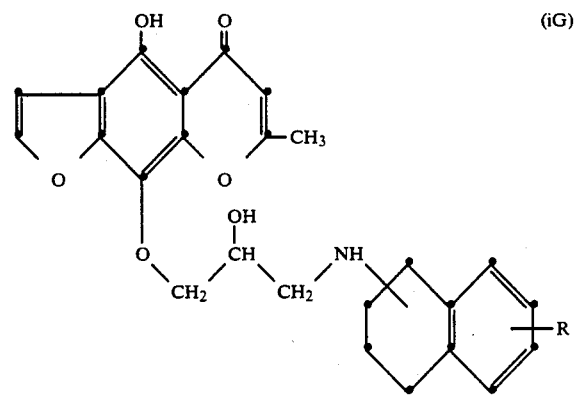
(iG)

wherein R is as defined above, and their salts with mineral or organic acids.

A preferred group of compounds of formula (i), wherein Ar has meaning (d), comprises those aryloxypropanolaminotetralins which can be represented by following formula (iH)

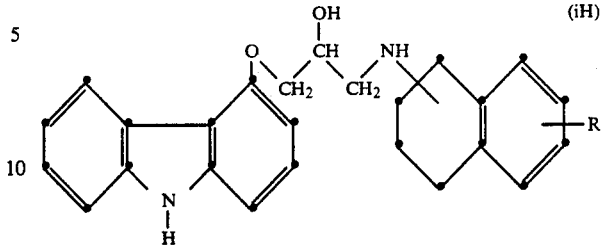
(iH)

wherein R is as defined above, and their salts with mineral or organic acids.

Among the compounds of formula (i), wherein Ar represents grouping (e), a preferred subclass comprises those aryloxypropanolaminotetralins which can be represented by following formula (iI)

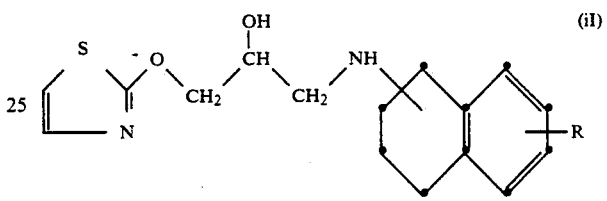
(iI)

wherein R is as defined above, as well as their salts with mineral or organic acids.

A preferred group of compounds of formula (i) wherein Ar has meaning (f) comprises those aryloxypropanolaminotetralins which can be represented by following formula (iJ)

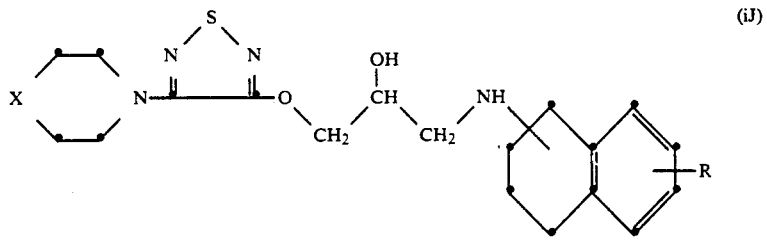
(iJ)

wherein R is as defined above and X represents an oxygen atom or a methylene group, as well as their salts with mineral or organic acids.

Among the compound of formula (i), according to the present invention there are comprised those wherein Ar represents the following preferred groups I to LXXVI

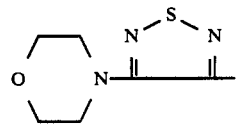
I

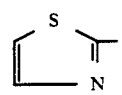
II

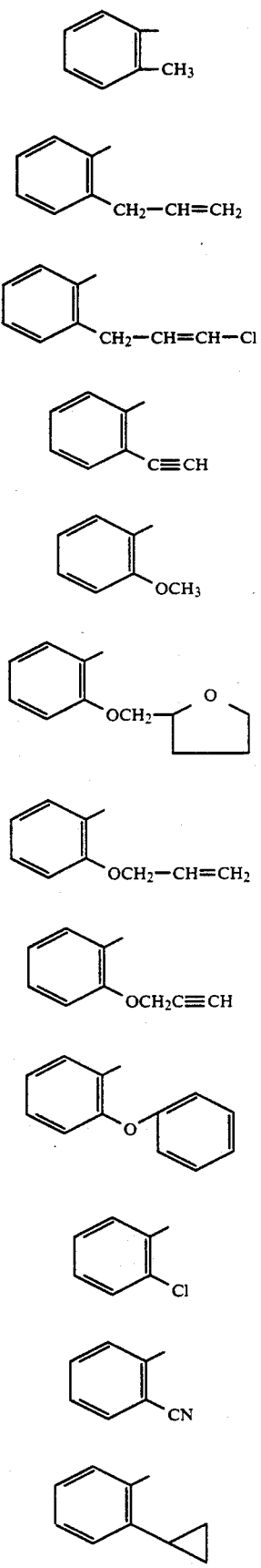
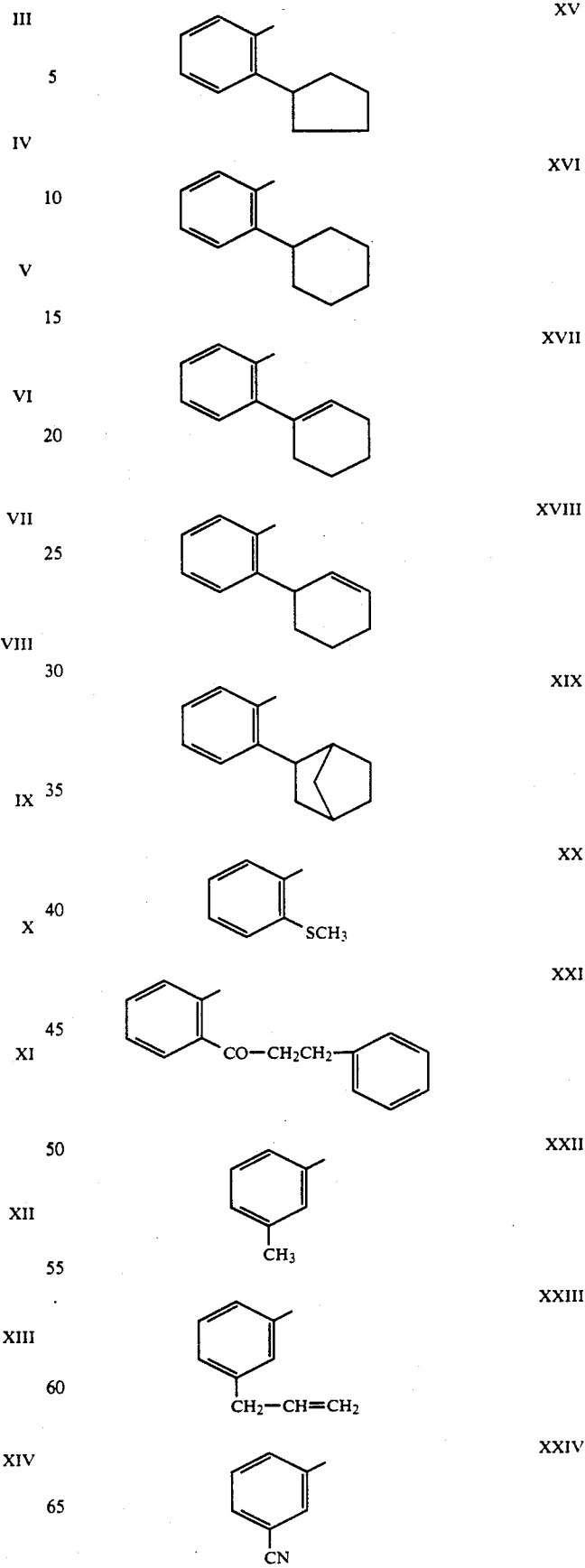

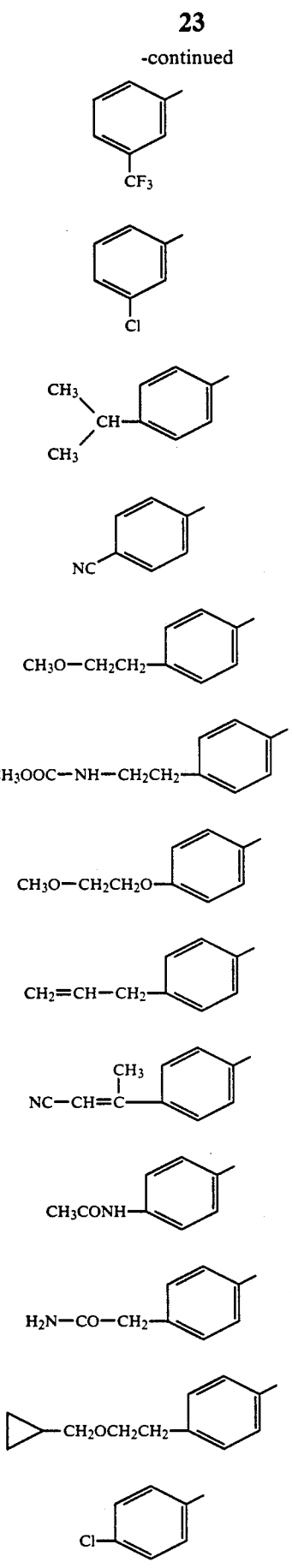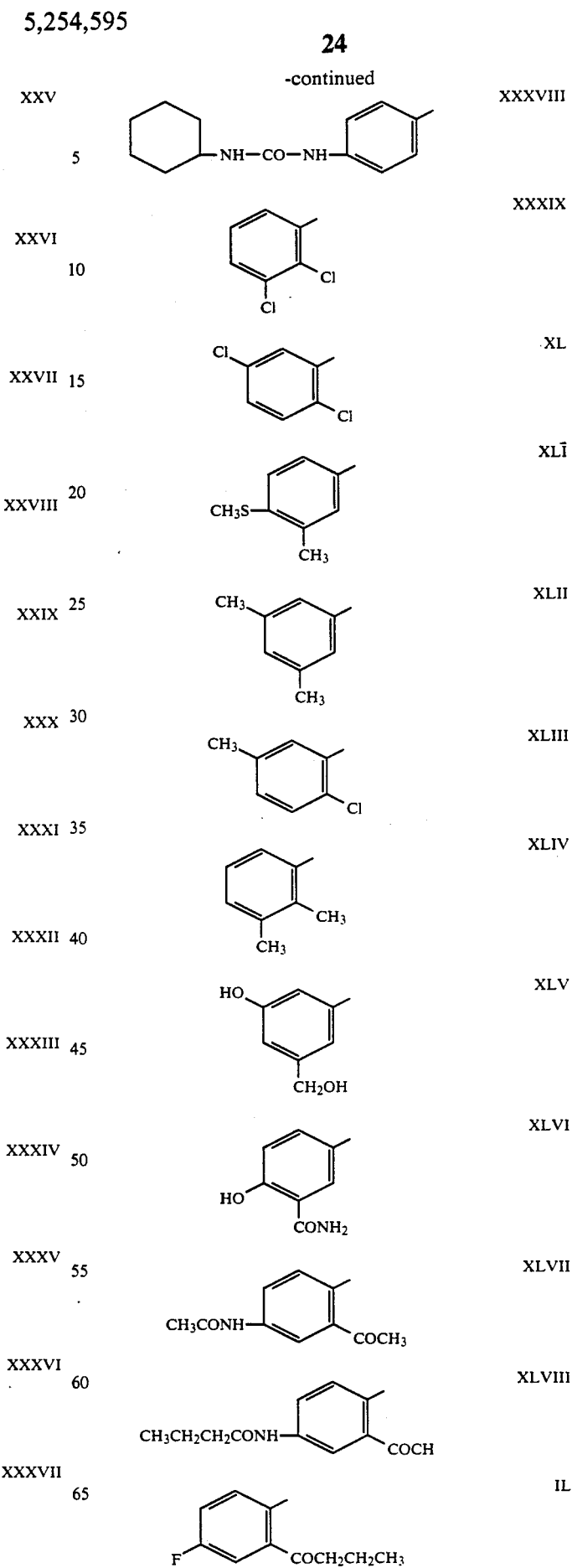

-continued
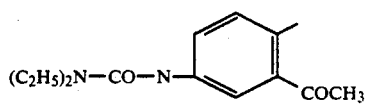 L
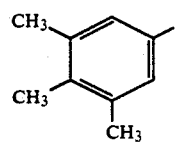 LI
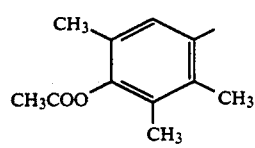 LII
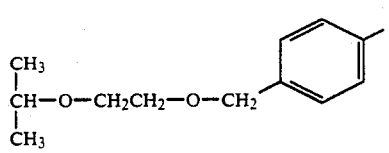 LIII
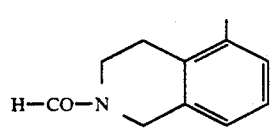 LIV
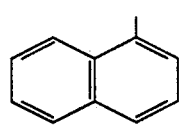 LV
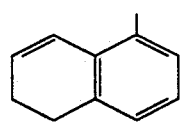 LVI
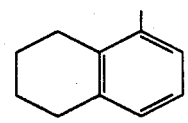 LVII
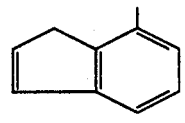 LVIII
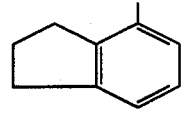 LIX
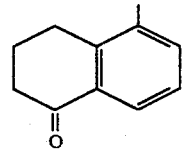 LX
-continued
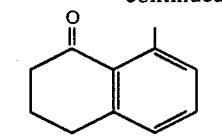 LXI
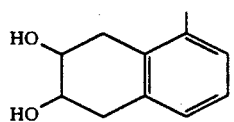 LXII
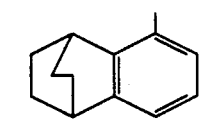 LXIII
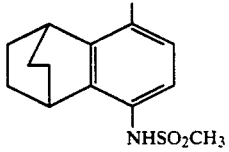 LXIV
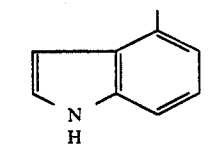 LXV
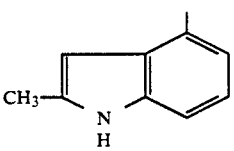 LXVI
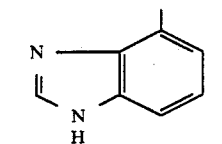 LXVII
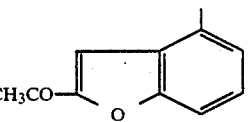 LXVIII
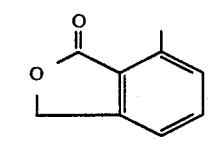 LXIX
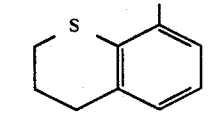 LXX
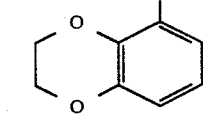 LXXI -continued

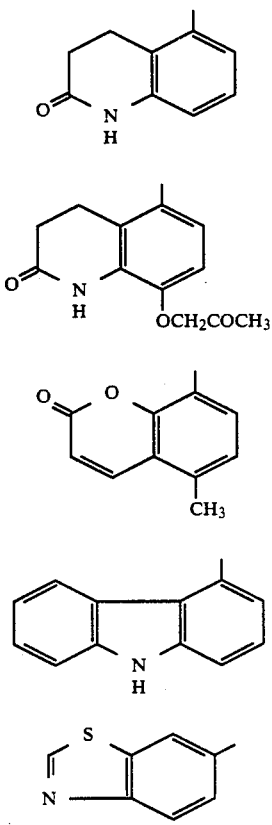

LXXII

LXXIII

LXXIV

LXXV

LXXVI

The compounds of above formula (i) can be either in an optically inactive form or in any optically active form including the enantiomers, the diastereoisomers and their mixtures. All these compounds and their salts do fall within the scope of the present invention.

As used therein, the terms "alkyl", "alkenyl" and "alkynyl" unless otherwise expressly specified designate monovalent hydrocarbon radicals containing up to 4 carbon atoms, which may be saturated or contain a double or triple bond such as methyl, ethyl, propyl, isopropyl, allyl, ethynyl and 2-propynyl.

The terms "alkoxy", "alkenyloxy" or "alkynyloxy" identify a hydroxy group substituted with an alkyl, alkenyl or alkynyl group as defined above.

The terms "alkanoyl" and "alkanoyloxy" identify, respectively, an alkylcarbonyl group and an hydroxy group substituted with an alkylcarbonyl group, wherein "alkyl" is as defined above.

The terms "tetralin" and "tetralone" refer to 1,2,3,4-tetrahydronaphthalene.

The term "aryloxypropanolaminotetralin" identifies a compound of formula (i) whose correct chemical name is N-(1,2,3,4-tetrahydronaphthyl)-3-aryloxy-2-hydroxypropanamine.

To avoid any uncertainty, in naming the compounds of formula (i), the position of attachment of the amino group to the tetralin moiety is either position 1- or 2-, and therefore the substituent R may be attached to any of positions 5-, 6-, 7- or 8-.

The terms "beta-antagonist" and "beta-blocker" have the following meaning "antagonist of the beta-adrenergic receptors".

The mineral or organic acids which form the acid addition salts according to the present invention include both those acids which give pharmaceutically acceptable salts such as the hydrochloride, the hydrobromide, the sulfate, the hydrogensulfate, the dihydrogenphosphate, the methanesulfonate, the methylsulfate, the maleate, the fumarate, the naphthalenesulfonate, and the like, and those acids which do not produce pharmaceutically acceptable salts but allow a suitable separation or crystallization of the compounds of formula (i), such as picric acid, oxalic acid, camphorsulphonic acids and the like.

Another object of the present invention is a process for the preparation of the aryloxypropanolaminotetralins of formula (i) and their salts, which comprises reacting an aryloxypropane of formula (ii)

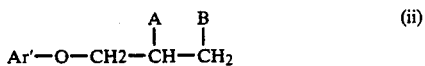

wherein Ar' has the same meaning as Ar above, but may contain —NH or —NH—, N-protecting groups, A is hydroxy and B is a halogen selected form chloro, bromo or iodo, or A and B taken together form an epoxy group, with an aminotetralin of formula (iii)

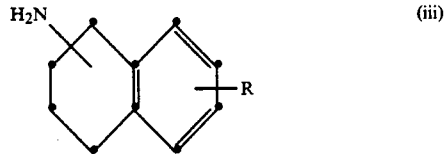

wherein R is as defined above, optionally in the presence of a tertiary amine; optionally deprotecting the obtained compound by removing the N-protecting group; when in the starting compound of formula (ii) Ar' represents a 2-acetamido-3-nitrophenyl or a 4-acetamido-3-nitrophenyl group, optionally deacetylating the obtained product by heating it in hydrochloric acid and optionally hydrogenating the obtained product in 97% formic acid in the presence of 10% Pd/C; and optionally converting the obtained product in one of its salts with mineral or organic acids.

As used herein the term "N-protecting group" designates an easily removable amino protecting group, such as formyl, an alkylcarbonyl group, e.g. acetyl or propionyl, an arylcarbonyl group such as benzoyl, an alkylsulfonyl group such as methanesulfonyl or an arylsulfonyl group such as benzenesulfonyl or p-toluenesulfonyl; preferred protecting groups are the arylsulfonyl groups and in particular benzenesulfonyl and p-toluenesulfonyl.

The reaction between the I-aryloxypropane (ii) and the aminotetralin (iii) is carried out by refluxing a solution of the two reactants in a suitable solvent such as a polar organic solvent e.g. dimethylsulfoxide or dimethylacetamide, or a lower alcohol, such as ethanol, n-propanol or isopropanol, optionally in the presence of a tertiary amine e.g. triethylamine or 1-methylpiperidine.

The optional removal of the N-protecting group of the thus obtained product is carried out according to conventional methods, as an example by refluxing a solution of the product in a suitably selected solvent such as a lower alcohol e.g. ethanol, n-propanol or isopropanol, in the presence of an alkali metal hydroxide such as sodium hydroxide.

When in the starting compound of above formula (ii) Ar' represents a 2-acetamido-3-nitrophenyl or 4-acetamido-3-nitrophenyl group, the thus obtained product may be deacetylated by heating it in a hydrochloric acid solution, preferably in 4N HCl, to afford a compound of formula (i) wherein Ar represents a 2-amino-3-nitrophenyl or 4-amino-3-nitrophenyl group. Furthermore the nitro group of these products may be catalytically hydrogenated (10% Pd/C) in 97% formic acid to afford reduction of the nitro group and simultaneous cyclysation of the diamino intermediate to the compound (i) wherein Ar is a 4- or a 5-benzimidazolyl group.

The thus obtained compound of formula (i) is isolated, as the free base or a salt thereof, by conventional techniques.

When the compound of formula (i) is obtained as the free base, salification is carried out by treatment with the selected acid in an organic solvent. Treatment of the free base dissolved for instance in an alcohol such as isopropanol, with a solution of the suitably selected acid in the same solvent, affords the corresponding addition salt which is isolated according to conventional techniques. This method can suitably be employed for the preparation of the hydrochloride, the hydrobromide, the sulfate, the hydrogensulfate, the dihydrogenphosphate, the methanesulfonate, the methylsulfate, the oxalate, the maleate, the fumarate, the naphthalene-2-sulfonate.

A the end of the reaction between the compound of formula (ii) and the aminotetralin of formula (iii), compound (i) may be isolated as one of its acid addition salts, e.g. as the hydrochloride or the oxalate; in this case, if necessary, the free base may be prepared by neutralization of said acid addition salt with a mineral or organic base such as sodium hydroxide or triethylamine or with an alkaline carbonate or bicarbonate such as sodium or potassium carbonate or bicarbonate.

The reactions involved in the above overall process do not alter the stereochemistry of the starting compounds. It is therefore possi-ble to apply the process of the present invention to the preparation of racemates as well as of optically pure isomers.

Accordingly, by reacting a 1-aryloxypropane (ii) racemate with an aminotetralin (iii) racemate, a mixture of stereoisomers RR, SS, RS and SR, is obtained. Analogously, by reacting an optically active 1-aryloxy-2,3-epoxypropane with an aminotetralin racemate, a couple of diastereoisomers of formula (i) is obtained, either (RR+RS) or (SS+SR), which can be separated into the single pure enantiomers (RR) and (RS) or (SS) and (SR). Preferably, when an optically active 1-aryloxy-2,3-epoxypropane is used, an aminotetralin of formula (iii) in optically active form is employed as the reaction partner, to afford an optically pure isomer.

The starting compounds of above formula (ii) are generally known products or they may be obtained by methods well known in the art. Typically, the general methods for preparing the compounds of formula (ii) are described in U.S. Pat. No. 3,501,769.

Accordingly, 1-aryloxypropanes of formula (ii), wherein A is hydroxy and B is halo, are prepared starting from the corresponding phenols Ar'OH and an epihalogenohydrin, preferably epichlorohydrin, in the presence of a tertiary amine.

Also the aryloxypropanes of formula (ii) wherein A and B, taken together represent an epoxy group, are prepared starting from the corresponding phenols Ar'OH, which need to be converted however into the corresponding alkaline salts (i.e. carrying out the reaction in the presence of an alkali hydroxide, e.g. sodium hydroxide, to provide a basic reaction medium) and epichlorohydrin.

The compounds of formula (ii), wherein A and B, taken together represent an epoxy group, in optically active form are prepared by known methods. More particularly they are prepared by the above general method starting from the corresponding phenol and the optically active epichlorohydrin, either (R) or (S) (J. Org. Chem. 1978, 43, 4876-4878). The epoxides having configuration (S) may also be prepared by the method described in DE 2,453,324.

As an example, the compounds of formula (ii) wherein Ar' is one of groups 1 to 67, are described in the documents listed hereinbelow: 1: U.S. Pat. No. 3,912,733; 2: DE 2 240 599; 3: DE 2 353 996; 4: DE 2 418 776; 5: BE 813.751; 6: BE 753.917; 7: BE 733.390;8: FR 1 588 855, DE 2 021 958; 9: U.S. Pat. No. 3,920,691; 10: NL 73/05478; 11: BE 794.669; 12: FR 1 466 164; 13: BE 724.929; 14: BE 754.860; 15: BE 764.659, BE 739.545; 16: CH 526 542, CH 526 544; 17: CH 527 188; 18: BE 793.073; 19: BE 765.313; 20: NL 72/14438; 21: DE 2 362 877; 22: BE 852.556; 23: JP 73–01070; 24: BE 783.440; 25: DE 2 620 179; 26: FR 2 042 378, DE 2 021 958; 27, 28, 29, 30, 47, 48, 49, 50, 51, 52, 53, 54, 55, 56, 57: J. Med. Chem., 1972, 15, 260–266; 31: U.S. Pat. No. 3,894,058; 32: DE 2 404 858; 33: BE 815.745; 34: FR 2 077 694; 35: JP 49-048649; 36: JP 49-094666; 37: NL 70/07503; 38: BE 753.840; 39: BE 773.205; 40: BE 739.545; 41: NL 69/011816; 42: BE 739.195; 43: DE 1 955 229; 44: JP 72-00055; 45: JP 49-051258; 46: NL 86/05887; 58: BE 863.622; 59: DE 2 711 382, BE 846.010; 60: BE 866.278; 61: BE 866.596; 62: DE 2 720 613; 63: U.S. Pat. No. 3,940,407; 64: DE 2 608 448; 65: BE 845.049; 66: JP 52-053868; 67: BE 853.949.

More particularly, the compounds of formula (ii) wherein Ar' is one of the above preferred groups I to LXXVII are described in the following documents: I: FR 2 009 110; II: FR 2 199 463; III: FR 2 023 556 or U.S. Pat. No. 3,501,769; IV, V, XXIII, XXXII: FR 1 479 614; VI: FR 1 510 271; VII: U.S. Pat. No. 3,501,769; VIII: FR 2 051 536; IX: FR 1 463 034; X: FR 1 583 559; XI, XII, XXII, XXVII: U.S. Pat. No. 3,501,769; XIII, XIV, XXVIII: FR 1 583 559, NL 67/17837; XIV: GB 1 294 159; XV: FR 1 575 615; XVI, XVII, XVIII: DE 2 636 725; XIX: FR 2 267 095 or FR 2 361 106; XX: FR 1 552 786; XXI: FR 2 144 601; XXII: FR 1 555 463 or U.S. Pat. No. 3,501,769; XXV, XXVI: U.S. Pat. No. 3,501,769; XXIX, XXX: FR 2 081 523; XXXI: FR 2 044 806; XXXIII: FR 2 353 520; XXXIV: FR 1 458 635; XXXV: FR 2 034 561; XXXVI: FR 2 330 383; XXXVII: U.S. Pat. No. 3,501,769; XXXVIII: FR 2 113 982; XXXIX: FR 2 261 001 or U.S. Pat. No. 3,501,769; XL: FR 2 130 284 or U.S. Pat. No. 3,501,769; XLI: FR 2 070 102; XLII: U.S. Pat. No. 3 501 769; XLIII: BE 691.159 or U.S. Pat. No. 3,309,406; XLIV: FR 2 073 434 or FR 2 215 419 or U.S. Pat. No. 3,501,769; XLV: U.S. Pat. No. 3,857,873; XLVI: U.S. Pat. No. 3 883 560; XLVII, XLVIII: GB 1 247 384; IL: FR 2 276 032; L: FR 2 255 058; LI: U.S. Pat. No. 3,501,769; LII: FR 1 567 149; LIII: BE 859.425, LIV: DE 2 620 179; LV: GB 994 918; LVI: FR 1 601 338; LVII: BE 641.417; LVIII: FR 2 035 816; LIX: FR 8298 M, BE 641.417; LX: FR 2 018 626 or BE 755.071; LXI: EP 67 106; LXII: FR 2 100 811, DE 2 258 995; LXIII: FR 2 059 580; LXIV: FR 2 157 897; LXV, LXVI: FR 1 466 164; LXVII: J. Med.

Chem., 1979, 22, 210–214, wherein the precursor 1-(2-acetamido-3-nitrophenoxy)-2,3-epoxypropane of formula (ii) wherein Ar is 2-acetamido-3-nitrophenyl, is described; LXVIII: FR 2 137 901; LXIX: FR 2 231 387; LXX: FR 2 092 004; LXXI: J. Med. Chem., 1972, 15, 260–266; LXXII: FR 2 179 715; LXXIII: FR 2 344 538; LXXIV: FR 2 042 378; LXXV: FR 2 196 165; LXXVI: FR 2 225 153.

The starting aminotetralins of formula (iii) are known compounds described in literature or they can be easily synthetized by reacting the appropriate 1- or 2-tetralones of formula (iv)

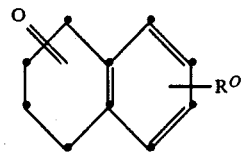
(iv)

wherein R° represents hydrogen or methoxy, with benzylamine, reducing the thus obtained benzylimino derivatives with sodium borohydride, removing the benzyl group by catalytic hydrogenation and, when in the starting compound of formula (iv) R° is methoxy, optionally demethylating the obtained methoxy-substituted aminotetralins with 48% HBr.

The two optically active forms of the aminotetralins (iii) can be prepared by resolution of the racemates according to well known procedures, e.g. salification with an optically active acid, preferably a mandelic acid.

The compounds of formula (i) are beta-receptor antagonists which are capable of inhibiting the intestinal beta-receptors and are characterized by a reduced activity on the cardiac and respiratory receptors (guinea pig right atrium and guinea pig trachea, respectively).

The antagonistic activity on beta-adrenergic receptors in isolated rat colon preparations has been assessed by the method described in EP-A-0255415. Said antagonistic activity has been proved both toward the classical beta-agonists, such as isoprenaline, and toward the selective ones, such as the compound coded SR 58375 A described in EP-A-0211721.

Beta-blocking activity on the cardiac and respiratory receptors has been evaluated by the conventional in vitro tests using isolated guinea pig atrial and tracheal preparations (Pharmacol. Res. Comm., 1988, 20, 147–151). In these tests the compounds of formula (i) proved to be poorly active.

More particularly, it has been shown that the compounds of formula (i) are much more active than the known beta-antagonists on rat colon isolates and much less active than the known compounds on atrium and trachea isolates. In view of these surprising properties of the compounds of above formula (i), their use as beta-antagonists for the treatment of non-cardiovascular and non-respiratory condi-tions, can be envisaged.

Furthermore, the compounds of formula (i) are poorly toxic; in particular their acute toxicity is compatible with their use as drugs, mainly for the treatment of gastrointestinal conditions, for the treatment and/or prophylaxis of glaucoma, as antimigraine, as psychotropic drugs, or in general for the treatment of those disorders where beta-antagonists have been considered, such as thyrotoxicosis, or hyperparathyroidism, in mammals.

For such a use, an effective amount of a compound of formula (i) or of a pharmaceutically acceptable salt thereof is administered to a mammal in need of such a treatement.

The compounds of formula (i) hereinabove as well as their pharmaceutically acceptable salts can be utilized in a daily dose of from 0.01 to 100 mg per kg of body weight of the mammal to be treated, preferably in a daily dose of from 0.1 to 50 mg/kg. In human beings, the daily dose may preferably vary from 0.5 mg to 5000 mg, more particularly from 2.5 to 2500 mg according to the age of the treated subject, to the type of treatment, prophylactic or curative, and to the severity of the disease. The compounds of formula (i) are generally administered in unit dosage forms of from 0.1 to 500 mg, preferably of from 0.5 to 250 mg of active ingredient, 1 to 5 times daily.

Said unit doses are preferably formulated in pharmaceutical compositions in which the active compound of formula (i) is in admixture with a pharmaceutical carrier.

Thus, according to another of its aspects, the present invention provides pharmaceutical compositions which comprise a compound of formula (i) hereinabove or one of its pharmaceutically acceptable salts as the active principle.

The pharmaceutical compositions of the present invention which contain the active ingredients of formula (i) preferably in association with a conventional pharmaceutical carrier, may be compounded in unit dosage forms suitable for the oral, sublingual, subcutaneous, intramuscular, intravenous, topical, transdermical or rectal administration route, for the treatment of the above disorders. Appropriate unit dosage forms of administration include the forms for oral administration, such as tablets, capsules, powders, granulates and oral solutions or suspensions and the forms for sublingual and buccal administration, the forms for parenteral administration useful for a subcutaneous, intramuscular or intravenous injection, as well as the forms for rectal administration.

When a solid composition is prepared in the form of tablets, the main active ingredient is mixed with a pharmaceutical excipient such as gelatine, starch, lactose, magnesium stearate, talc, arabic gum and the like. Tablets may be coated with sucrose or other suitable materials or they may be treated so that their activity is extended or delayed and that they continually release a predetermined amount of active ingredient.

A preparation in capsules is obtained by mixing the active ingredient with a diluent and a lubricant and by filling soft or hard capsules with the mixture thus obtained.

A liquid preparation in the form of syrup or elixir or for the administration in drops may contain the active ingredient together with a possibly acaloric sweetening agent, methylparaben and propylparaben as antiseptics, as well as a flavoring agent and an appropriate coloring agent.

Water-dispersible powders or granulates may contain the active ingredient mixed with dispersing agents or wetting agents, or suspending agents such as polyvinylpyrrolidone and the like, and with sweetening or flavoring agents.

For topical administration the active principle can be admixed with an excipient suitable for the preparation of creams or ointments or it is dissolved in a vehicle suitable for intraocular administration, for example as a collyrium.

For rectal administrations, suppositories are prepared with binding agents melting at rectal temperature, for example, cocoa butter or polyethyleneglycols.

For parenteral administration, aqueous suspensions, isotonic saline solutions or sterile injectable solutions are used, which contain pharmacologically compatible dispersing and/or wetting agents, for example propyleneglycol or butyleneglycol.

The active ingredient may also be formulated in the form of microcapsules, possibly with one or more supports or additives.

The compounds of formula (i), typically those isotopically labelled, may also be employed as laboratory tools in biochemical tests.

The compounds of formula (i) in fact bind selectively to a beta-adrenergic receptor which is present in the mammalian intestinal tract and which is distinct from the generally recognized beta-1 and beta-2 receptors. These compounds can therefore be employed in a conventional binding assay, using the isolated rat colon wherein said atypical receptor is particularly abundant and determining the amount of compound (i) displaced by the compound to be assayed for receptor binding activity, in order to evaluate the affinity of said compound to the binding sites of this particular beta-receptor.

Combining this biochemical assay with other conventional binding assays aimed at evaluating the affinity of the test compounds to the beta-1 and beta-2 receptors, it is possible to screen out those compounds which may elicit a specific effect on the intestinal tract without producing any cardiac or respiratory side-effect.

A further specific object of the present invention is therefore a reagent suitable for use in biochemical assays to differentiate the beta-adrenergic receptors, which comprises at least one of the compounds of formula (i), suitably labelled.

The following examples further illustrate the invention without however limiting it. The symbol of the rotatory power, which is indicated as /alpha/ should read as $[alpha]_D^{20}$. Chromatographies have been carried out on MERCK 70-230 mesh silica gel columns.

PREPARATION I 2-amino-7-hydroxytetralin hydrobromide (a) A mixture of 7-methoxy-2-tetralone (8 g), benzylamine (4.8 g), anhydrous toluene (150 ml) and p-toluenesulfonic acid (100 mg) is heated to the reflux temperature for 3 hours. The solvent is then evaporated off and the oily residue is taken up in methanol (100 ml). Sodium borohydride (8.5 g) is cautiously added to the thus obtained solution maintained at 0°-5° C. The reaction mixture is stirred overnight at room temperature, water (50 ml) is then added thereto and stirring is prolonged for additional 30 minutes. The solvent is evaporated off and the residue is taken up in water (30 ml) and concentrated ammonium hydroxide (10 ml). The aqueous solution is extracted with ethyl acetate (200 ml), the organic phase is dried over sodium sulfate and concentrated to dryness, yielding a dark oil which is purified by flash chromatography eluting with ethyl acetate/methanol 95/5. The thus obtained base is then converted into the corresponding hydrochloride by dissolving it into isopropanol (40 ml) and adding thereto with hydrogen chloride saturated isopropanol. 2-Benzylamino-7-methoxy-1,2,3,4-tetrahydronaphthalene hydrochloride (11.4 g) is thus obtained; m.p. 265°-267° C. (dec.).

(b) The above product is dissolved in a mixture methanol (200 ml)/ water (100 ml) and hydrogenated in the presence of 10% Pd/C (1.2 g) at atmospheric pressure and 45°-50° C. After 4 hours, the reaction mixture is filtered and the solvent is evaporated off. The residue is taken up in absolute ethanol and the ethanol is evaporated off. After repeating this last procedure, a white solid is obtained which is taken up in hot isopropanol (70 ml). Upon cooling a precipitate is obtained which is recovered by filtration yielding 2-amino-7-methoxytetralin hydrochloride (7.8 g); m.p. 214°-216° C.

(c) The above product (6.6 g) is suspended into 48% hydrobromic acid (80 ml) and the reaction mixture is refluxed for 2 hours. The obtained solution is concentrated to dryness, the residue is taken up in absolute ethanol and the solvent is evaporated off twice. The obtained oil is dissolved in hot isopropanol (20 ml) and ethyl ether (30 ml) is then added thereto to precipitate 2-amino-7-hydroxytetralin hydrobromide as a crystalline product 86.8 g); m.p. 171°-173° C.

PREPARATION II

R(+)-2-amino-7-hydroxytetralin monohydrate.

A solution of (+) mandelic acid (43 g) in absolute ethanol (550 ml) is added to a solution of raw 2-amino-7-methoxytetralin (50 g), free base, obtained from the corresponding hydrochloride (PREPARATION I (b)) by neutralisation with 10% sodium hydroxide and extraction with ethyl acetate followed by evaporation of the solvent, in absolute ethanol (550 ml). The precipitate which is obtained upon standing overnight at room temperature, is recovered by filtration and crystallized twice from absolute ethanol, each time recovering the product crystallized upon standing at room temperature overnight. The pure salt of (+)-2-amino-7-methoxytetralin with (+) mandelic acid (34.2 g, 74%) is thus obtained; m.p. 190°-192° C. (The mother liquors of the first crystallization are separately recovered and used in the following PREPARATION III). The obtained salt (34 g) is suspended in water (300 ml) and the suspension is basified by the addition of 1N NaOH. The aqueous phase is extracted with ethyl acetate, the organic phase is concentrated to dryness and the residue is taken up in 48% hydrobromic acid (260 ml). The reaction mixture is then heated at reflux for 3 hours and concentrated to dryness under vacuum. The obtained residue is taken up in water (70 ml), the aqueous solution is basified by the addition of concentrated ammonium hydroxide and cooled overnight. The thus obtained R(+)-2-amino-7-hydroxytetralin monohydrate (17 g) is then recovered by filtration; m.p. 143°-144° C., /alpha/ =+85.1° (methanol, c=0.5%).

The corresponding hydrochloride has a rotatory power which corresponds to that reported in the literature (Molecular Pharmacology, 1982, 22, 281-289).

PREPARATION III

S(−)-2-amino-7-hydroxytetralin monohydrate

The mother liquors of the first crystallization described in PREPARATION II are concentrated to dryness and the obtained residue is suspended in water (300 ml). 1N NAOH is then added thereto to afford a basic solution and ethyl acetate is used to extract the free base therefrom. By following the procedure described in PREPARATION II but starting from the thus obtained base and (−) mandelic acid, the (−)-2-amino-7-methoxytetralin salt with (−) mandelic acid (m.p. 189°-191° C.) is obtained which, upon neutralization and demethylation with hydrobromic acid, gives S(−)-2-amino-7-hydroxytetralin monohydrate (17 g); m.p. 143°-144° C., /alpha/ = −86.9° (methanol, c=0.5%).

The corresponding hydrochloride has a rotatory power which corresponds to that reported in the literature (Molecular Pharmacology 1982, 22, 281-289).

EXAMPLE 1

A solution of 2-amino-7-hydroxytetralin (3 g) obtained from the corresponding hydrobromide described in PREPARATION I by neutralization with ammonium hydroxide and extraction with ethyl acetate/ethanol 9/1 v/v, and 1-naphthyloxy-2,3-epoxypropane (3.68 g) in ethanol (80 ml) is refluxed for 5 hours. The reaction mixture is then allowed to cool down to room temperature, the solvent is evaporated off under reduced pressure and the oily residue is purified by silica gel column chromatography eluting first with ethyl acetate, up to complete elution of the first spot, and then with ethyl acetate/ethanol 9/1 v/v, up to complete elution of the product. Those fractions which contain the desired product are pooled and concentrated under reduced pressure. The residue is dissolved in hot isopropanol (25 ml), the solution is acidified by the addition of hydrochloric acid in isopropanol and the crystalline precipitate is recovered by filtration yielding 3.6 g of N-(7-hydroxy-1,2,3,4-tetrahydronaphth-2-yl)-2-hydroxy-3-(1-naphthyloxy)propanamine hydrochloride; m.p. 184°-187° C.

EXAMPLE 2

A solution of 2-aminotetralin (3.2 g) obtained from the corresponding hydrochloride by neutralisation with NAOH and extraction with ethyl acetate, and 1-naphthyloxy-2,3-epoxypropane (4.34 g) in absolute ethanol (90 ml) is refluxed for 6 hours. The organic solvent is then evaporated off, the obtained residue is dissolved in isopropanol (50 ml) and the solution is acidified by the addition of HCl/isopropanol. The precipitate is recovered by filtration and crystallized from 95% ethanol (150 ml) yielding 3 g of N-(1,2,3,4-tetrahydronaphth-2-yl)-2-hydroxy-3-(1-naphthyloxy)propanamine hydrochloride; m.p. 209°-212° C.

EXAMPLE 3

A solution of 1-aminotetralin (2.65 g) and 1-naphthyloxy-2,3-epoxypropane (3.6 g) in absolute ethanol (80 ml) is refluxed for 6 hours, the reaction solvent is then evaporated off under reduced pressure and the obtained oil is purified by silica gel column chromatography eluting with ethyl acetate up to complete elution of the reaction product. Fractions containing the desired product are pooled and evaporated under reduced pressure. The obtained product is dissolved in isopropanol (40 ml) and the solution is acidified by the addition of hydrochloric acid in isopropanol. The thus obtained precipitate is recovered by filtration and crystallized from 95% ethanol (70 ml) yielding 2.5 g of N-(1,2,3,4-tetrahydronaphth-1-yl)-2-hydroxy-3-(1-naphthyloxy)-propanamine hydrochloride; m.p. 179°-183° C.

EXAMPLE 4

A solution of 2-amino-7-hydroxytetralin (4.7 g) and 1-(2-allyl)-phenoxy-2,3-epoxypropane (5.48 g) in absolute ethanol (120 ml) is heated to the reflux temperature for 5 hours. The solvent is then evaporated off, the residue is dissolved in isopropanol and the solution is acidified by the addition of HCl isopropanol. After 30 minutes at 0°-5° C., the obtained precipitate is recovered by filtration, washed with isopropyl ether and dried in the oven. Upon crystallization from absolute ethanol (250 ml), 3.1 g of N-(7-hydroxy-1,2,3,4-tetrahydronaphth-2-yl)-2-hydroxy-3-(2-allylphenoxy)propanamine hydrochloride are obtained; m.p. 232°-235° C.

EXAMPLE 5

Operating as described in Example 2 but replacing 1-naphthyloxy-2,3-epoxypropane with 1-(2-allyl)-phenoxy-2,3-epoxypropane, a product is obtained which, upon crystallization from absolute ethanol affords N-(1,2,3,4-tetrahydronaphth-2-yl)-2-hydroxy-3-(2-allylphenoxy)-propanamine hydrochloride; m.p. 175°-177° C.; yield 57%.

EXAMPLE 6

A solution of 1-aminotetralin (2.5 g) and 1-(2-allyl-phenoxy)-2,3-epoxypropane (3.23 g) in ethanol (70 ml) is refluxed for 5 hours and then evaporated under reduced pressure yielding an oily residue which is applied to a silica gel column developed with ethyl acetate up to complete elution of the product containing fractions. Said fractions are pooled and evaporated under reduced pressure to afford an oil which is then dissolved in ethyl ether (50 ml). Upon the addition of a solution of oxalic acid (1.1 g) in acetone (10 ml), a precipitate forms which is recovered by filtration and crystallized from 95% ethanol yielding 3.0 g of N-(1,2,3,4-tetrahydronaphth-1-yl)-2-hydroxy-3-(2-allylphenoxy)propanamine oxalate; m.p. 163°-165° C.

EXAMPLE 7

A mixture of 1-[1-(p-toluenesulfonyl)indol-4-yloxy]-2,3-epoxypropane (20 g), prepared as described in EP-A-228356, and 2-amino-7-hydroxytetralin (10.5 g) in isopropanol (300 ml) is heated to the reflux temperature for 4 hours. The solvent is then evaporated off under reduced pressure, the residue is dissolved in ethyl acetate and the organic solution is washed with water, dried over sodium sulfate and evaporated under reduced pressure. The residue is taken up first in ethanol (200 ml) and then in a solution of sodium hydroxide (15 g) in water (90 ml). The reaction mixture is heated to the reflux temperature for 4 hours, made slightly acidic by the addition of 1N HCl and then basified by the addition of concentrated ammonium hydroxide. The reaction mixture is concentrated under reduced pressure, the residue is taken up in absolute ethanol and concentrated to dryness and this last procedure is repeated. The obtained residue is taken up in ethanol, filtered and washed on filter with ethanol. The filtrate and the washing ethanol are combined and the solution is basified by the addition of concentrated ammonium hydroxide. The residue which is obtained by evaporating off the solvent is purified by silica gel column chromatography eluting first with ethyl acetate and then with a mixture ethyl acetate/reethanol 9/1 v/v. The product-containing fractions are combined and evaporated to dryness. A mixture of acetic acid and isopropanol is used to take up the product. The precipitate which forms is then recovered by filtration and crystallized from 95% ethanol (60 ml) affording 2.6 g of N-(7-hydroxy-1,2,3,4-tetrahydronaphth-2-yl)-2-hydroxy-3-indol-4-yloxypropanamine acetate; m.p. 167°-170° C.

EXAMPLE 8

A mixture of R(+)-2-amino-7-hydroxytetralin monohydrate (6.5 g), obtained as described in PREPARATION II, and 1-[1-(p-toluenesulfonyl)indol-4-yloxy]-2,3-epoxypropane (12.45 g) in isopropanol (200 ml) is heated to the reflux temperature for 4 hours, the solvent is then evaporated off under reduced pressure and the obtained residue is dissolved in ethyl acetate. The organic solution is washed with water, dried over sodium sulfate and evaporated under reduced pressure. The residue is taken up in ethanol (150 ml) and in a solution of sodium hydroxide (10 g) in water (60 ml). The reaction mixture is refluxed for 4 hours, made slightly acidic by the addition of 1N HCl and then basified by the addition of concentrated ammonium hydroxide. The reaction mixture is then concentrated under reduced pressure, the obtained residue is taken up in absolute ethanol and concentrated to dryness, this last procedure being repeated twice. The residue is finally taken up in ethanol. Sodium chloride is filtered off and washed with ethanol. The filtrate and the ethanol washing are combined, and the solution is made basic by the addition of concentrated ammonium hydroxide and concentrated to dryness. The residue is purified by silica gel column chromatography eluting with a mixture methylene chloride/ethanol 9/1 v/v. The product-containing fractions are pooled and evaporated to dryness yielding 1 g of N-[(R)-7-hydroxy-1,2,3,4-tetrahydronaphth-2-yl]-(RS)-2-hydroxy-3-indol-4-yloxypropanamine as a vitrous solid.

NMR (DMSO-d6): 7.1 (1H, dd , J≈J2=2 Hz, CH alpha), 10.9 (OH+NH)δ

EXAMPLE 9

A solution of 2-amino-6-hydroxytetralin (2.6 g) and 1-naphthyloxy-2,3-epoxypropane (3.2 g) in ethanol (80 ml) is refluxed for 5 hours, and then allowed to cool to room temperature. The solvent is evaporated off under reduced pressure and the thus obtained oil is chromatographed on a silica gel column eluting first with ethyl acetate up to complete elution of the first spot, and then with a mixture ethyl acetate/reethanol 9/1 v/v up to complete elution of the product. The fractions are pooled and concentrated under reduced pressure. The residue is dissolved in isopropanol (20 ml) and a solution of fumaric acid (0.95 g) in isopropanol (10 ml) is then added thereto. The precipitate is recovered by filtration, washed with ethyl ether and dissolved in water. A concentrated sodium hydroxide solution is then added thereto up to a basic pH and the solution is extracted with ethyl acetate. The organic extract is dried over sodium sulfate and concentrated to dryness. The residue is triturated with a small amount of ethyl acetate and filtered yielding 1.9 g of N-(6-hydroxy-1,2,3,4-tetrahydronaphth-2-yl)-2-hydroxy-3-(1-naphthyloxy)propanamine; m.p. 118°-120° C.

EXAMPLE 10

A solution of 2-amino-7-hydroxytetralin (2.45 g) and 1-(2-methylphenoxy)-2,3-epoxypropane (2.5 g) in ethanol (75 ml) is refluxed for 5 hours. Ethanol is evaporated off, the residue is taken up in acetone (20 ml) and the solution is made acidic by the addition of HCl isopropanol. The precipitate which forms is recovered by filtration, washed with ethyl ether and crystallized from 95% ethanol (30 ml), affording 1.7 g of N-(7-hydroxy-1,2,3,4-tetrahydronaphth-2-yl)-2-hydroxy-3-(2-methylphenoxy)propanamine hydrochloride m.p. 224°-226° C.

EXAMPLE 11

Following the procedure described in Example 2, but replacing 1-naphthyloxy-2,3-epoxypropane with 1-(2-methylphenoxy)-2,3-epoxypropane, and crystallizing the obtained product from absolute ethanol, N-(1,2,3,4-tetrahydronaphth-2-yl)-2-hydroxy-3-(2-methylphenoxy)-propanamine hydrochloride is afforded; m.p. 180°-182°-C.

EXAMPLE 12

A solution of 1-aminotetralin (2.95 g) and 1-(2-methylphenoxy)-2,3-epoxypropane (3.3 g) in ethanol (80 ml) is heated to the reflux temperature for 5 hours. Ethanol is then evaporated off and the residue is applied to a silica gel column, developed with a mixture ethyl acetate/cyclohexane 7/3 v/v. The combined fractions are evaporated to dryness and the residue is taken up in isopropanol (40 ml). The solution is made acidic by the addition of HCl isopropanol, then isopropyl ether (40 ml) is added thereto and the reaction mixture is allowed to stand for 2 hours at 0°-5° C. The precipitate is recovered by filtration and crystallized from isopropanol (20 ml) yielding 2.5 g of N-(1,2,3,4-tetrahydronaphth-1-yl)-2-hydroxy-3-(2-methylphenoxy)propanamine hydrochloride; m.p. 123°-124° C.

EXAMPLE 13

(a) A solution of 1-[1-(p-toluenesulfonyl)indol-4-yloxy]-2,3-epoxypropane (3.9 g) and 2-amino-7-methoxytetralin (2.2 g) in isopropanol (40 ml) is refluxed for 3 hours. The reaction mixture is then evaporated to dryness, the residue is dissolved in ethyl acetate and the obtained solution is washed with water, dried over sodium sulfate and evaporated to dryness. The residue is taken up in ethyl acetate/isopropanol and the obtained solution is made acidic by the addition of HCl/isopropanol. The precipitate which forms is recovered by filtration, and suspended in hot ethanol. The suspension is then cooled and filtered and the solid recovered by filtration is dried yielding 3.1 g of N-(7-methoxy-1,2,3,4-tetrahydronaphth-2-yl)-2-hydroxy-3-[1-(p-toluenesulfonyl)indol-4-yloxy]propanamine hydrochloride; m.p. 228°-231° C.

(b) A mixture containing the above product (12.5 g), and sodium hydroxide (5.4 g) in water (34 ml) and 95% ethanol (76 ml) is refluxed for 4 hours and then cooled to room temperature. Ethyl acetate (400 ml) is then added thereto and the organic phase is separated, washed with water, dried over sodium sulfate and evaporated to dryness. The residue is purified by silica gel column chromatography eluting with a mixture ethyl acetate/methanol 95/5 v/v. The fractions containing the pure product are pooled and evaporated to dryness yielding 6 g of N-(7-methoxy-1,2,3,4-tetrahydronaphth-2-yl)-2-hydroxy-3-(indol-4-yloxy)propanamine as an amorphous solid.

NMR (DMSO-d6): 3.68 (3H, s, —OCH3), 7.2 (1H, dd, J1≈J2=2 Hz, CH alpha)

EXAMPLE 14

A mixture of 1-aminotetralin (2.94 g) and 1-(2-methoxyphenoxy)-2,3-epoxypropane (3.6 g) and absolute ethanol (100 ml) is refluxed for 5 hours. The solvent is then evaporated off under reduced pressure, the residue is chromatographed on a silica column eluting with ethyl acetate. The obtained fractions are combined and evaporated to dryness and the residue is taken up in a mixture hexane/isopropyl ether 1/1 v/v and filtered. The solid on filter is crystallized from ethyl acetate yielding 2 g of N-(1,2,3,4-tetrahydronaphth-1-yl)-2-hydroxy-3-(2-methoxyphenoxy)propanamine; m.p. 99°–102° C.

EXAMPLE 15

A solution of 2-aminotetralin (2.2 g) and 1-(2-methoxyphenoxy)-2,3-epoxypropane (2.7 g) in ethanol (70 ml) is refluxed for 5 hours and the solvent is then evaporated off under reduced pressure. The residue is taken up in isopropanol and the hot stirred solution is acidified by the addition of HCl/isopropanol. The precipitate is recovered by filtration yielding 2.1 g of N-(1,2,3,4-tetrahydronaphth-2-yl)-2-hydroxy-3-(2-methoxyphenoxy)propanamine hydrochloride; m.p. 140°–143° C.

EXAMPLE 16

A mixture of 2-amino-6-hydroxytetralin (0.9 g) and 1-(2-methoxy)-phenoxy-2,3-epoxypropane (1 g) in absolute ethanol (30 ml) is refluxed for 5 hours. The solvent is then evaporated under reduced pressure and the residue is purified by silica gel column chromatography eluting first with ethyl acetate and then with a mixture ethyl acetate/methanol 9/1 v/v. The fractions containing the product are pooled and evaporated to dryness, the obtained residue is dissolved in acetone and the hot solution is acidified by stirring in HCl/isopropanol. The precipitate is recovered by filtration yielding 0.25 g of N-(6-hydroxy-1,2,3,4-tetrahydronaphth-2-yl)-2-hydroxy-3-(2-methoxyphenoxy)propanamine hydrochloride; m.p. 146°–148° C.

EXAMPLE 17

A mixture of 2-amino-7-hydroxytetralin (3.15 g) and 1-(2-methoxy)-phenoxy-2,3-epoxypropane (3.45 g) in absolute ethanol (100 ml) is refluxed for 5 hours. The solvent is then evaporated under reduced pressure and the residue is chromatographed on a silica gel column eluting first with ethyl acetate and then with a mixture ethyl acetate/methanol 85/15 v/v. The combined fractions are evaporated to dryness, the oily residue is dissolved in absolute ethanol and acidified by the addition of HCl/isopropanol. The precipitate is then recovered by filtration yielding 2 g of N-(7-hydroxy-1,2,3,4-tetrahydronaphth-2-yl)-2-hydroxy-3-(2-methoxyphenoxy)propanamine hydrochloride; m.p. 173°–176° C.

EXAMPLE 18

A mixture of 1-aminotetralin (5.15 g) and 1-(2-allyloxy)-phenoxy-2,3-epoxypropane (7.22 g) in absolute ethanol (80 ml) is refluxed for 5 hours, the solvent is evaporated off under reduced pressure and the residue is chromatographed on a silica gel column eluting with a mixture ethyl acetate/cyclohexane 7/3 v/v. The pooled fractions are evaporated to dryness under reduced pressure, the residue is triturated in a very small amount of ethyl ether, filtered and crystallized from isopropyl ether yielding 2.1 g of N-(1,2,3,4-tetrahydronaphth-1-yl)-2-hydroxy-3-(2-allyloxyphenoxy)propanamine; m.p. 72°–75° C.

EXAMPLE 19

A mixture of 2-aminotetralin (2.2 g) and 1-(2-allyloxy)-phenoxy-2,3-epoxypropane (3.1 g) in absolute ethanol (80 ml) is reflux for 5 hours. The solvent is evadorated off and the residue is purified by a silica gel column chromatography eluting first with ethyl acetate and then with a mixture ethyl acetate/methanol 9/1 v/v. The product-containing fractions are pooled and evaporated to dryness and the obtained residue is taken up in ethyl ether and filtered yielding 2.6 g of N-(1,2,3,4-tetrahydronaphth-2-yl)-2-hydroxy-3-(2-allyloxyphenoxy)propanamine; m.p. 98°–100° C.

EXAMPLE 20

A mixture of 2-amino-7-hydroxytetralin (3.4 g) and 1-(2-allyloxy)phenoxy-2,3-epoxypropane (4.12 g) is dissolved in absolute ethanol (50 ml) and the obtained solution is heated to the reflux temperature for 5 hours. Ethanol is then evaporated off and the obtained residue is chromatographed on a silica gel column eluting first with ethyl acetate and then with a mixture ethyl acetate/methanol 9/1 v/v. The fractions which contain the desired product are pooled and evaporated to dryness, the thus obtained oily residue is dissolved in isopropanol and the solution is made acidic by the addition of HCl/isopropanol. The precipitate which forms is recovered by filtration and crystallized from absolute ethanol affording 3.1 g of N-(7-hydroxy-1,2,3,4-tetrahydronaphth-2-yl)-2-hydroxy-3-(2-allyloxyphenoxy)-propanamine hydrochloride; m.p. 183°–185° C.

EXAMPLE 21

A mixture of 2-amino-6-hydroxytetralin (2.6 g) and 1-(2-allyloxyphenoxy)-2,3-epoxypropane (3.3 g) in absolute ethanol (80 ml) is refluxed for 5 hours, the solvent is then evaporated off under reduced pressure and the residue is chromatographed on a silica gel column eluting first with ethyl acetate and then with a mixture ethyl acetate/methanol 9/1 v/v. The combined fractions are evaporated to dryness, the obtained residue is dissolved in isopropanol, and the solution is acidified by the addition of HCl/isopropanol. The precipitate which forms is recovered by filtration and crystallized from isopropanol yielding 2.1 g of N-(6-hydroxy-1,2,3,4-tetrahydronaphth-2-yl)-2-hydroxy-3-(2-allyloxyphenoxy)-propanamine hydrochloride; m.p. 145°–147° C.

EXAMPLE 22

A mixture of 1-aminotetralin (5.15 g) and 1-[1-(p-toluenesulfonyl)indol-4-yloxy]-2,3-epoxypropane (12 g) in absolute ethanol (150 ml) is refluxed for 6 hours. The solvent is then evaporated off and the oily residue is dissolved in absolute ethanol (100 ml). A solution of sodium hydroxide (7.5 g) in water (30 ml) is added thereto. The obtained reaction mixture is refluxed for 6 hours and then evaporated under reduced pressure. The residue which is obtained is then dissolved in ethyl acetate (150 ml), the organic solution is thoroughly washed with water, dried over sodium sulfate, and filtered. Ethyl acetate is then evaporated off and the obtained oily residue is chromatographed on a silica gel column eluting with a mixture ethyl acetate/cyclohexane 7/3 v/v. The combined fractions are evaporated to dryness, the oily residue is taken up in a very small amount of ethyl ether which is then removed under vacuum yielding 1.5 g of N-(1,2,3,4-tetrahydronaphth-1-yl)-[2-hydroxy-3-(4-indolyloxy)propanamine, as a vitreous solid.

IR(KBr): 3404, 2926, 1361, 1244, 1092, 740 cm-1

EXAMPLE 23

A mixture of 2-amino-6-hydroxytetralin (3.26 g) and 1-[1-(p-toluenesulfonyl)indol-4-yloxy]-2,3-epoxypropane (6.8 g) in absolute ethanol (80 ml) is refluxed for 5 hours. The solvent is then evaporated off and the residue is suspended in absolute ethanol (185 ml). A solution of sodium hydroxide (4.8 g) in water (55 ml) is then added thereto and the reaction mixture is refluxed for 6 hours. The solvent is evaporated off under reduced pressure, the residue is dissolved in ethyl acetate (200 ml) and the obtained solution is washed twice with water, dried over sodium sulfate and evaporated under reduced pressure. The obtained residue is chromatographed on a silica gel column eluting first with ethyl acetate and then with a mixture ethyl acetate/methanol 85/15 v/v. The fractions containing pure product are pooled and the solvent is evaporated, the residue is taken up with ethyl ether and filtered yielding 2.4 g of N-(6-hydroxy-1,2,3,4-tetrahydronaphth-2-yl)-2-hydroxy-3-(4-indolyloxypropanamine); as a vitreous solid.

NMR (DMSO-d6): 7.15 (1H, dd, J1≃J2=2 Hz), CH alpha), 10.9 (OH+NH)δ. IR(KBr): 3408, 2923, 1501, 1240, 742 cm-1

EXAMPLE 24

A mixture of 2-aminotetralin (5 g) and 1-[1-(p-toluenesulfonyl)-indol-4-yloxy]-2,3-epoxypropane (11.7 g) in absolute ethanol (150 ml) is refluxed for 6 hours. The solvent is evaporated, the obtained residue is dissolved under stirring in hot isopropanol (100 ml) and the solution is made acidic by the addition of hydrochloric acid in isopropanol. The precipitate which forms is recovered by filtration, dissolved in a mixture of ethanol (250 ml) and aqueous sodium hydroxide (7.6 g in 85 ml of water). The reaction mixture is refluxed for 6 hours, the solvent is evaporated off and the residue is dissolved in ethyl acetate (200 ml). The obtained solution is washed twice with water, dried over sodium sulfate and concentrated by evaporating off the solvent. The residue is chromatographed on a silica gel column eluting with ethyl acetate. The fractions containing pure product are pooled. The solvent is evaporated and the residue is dissolved in ethyl ether (20 ml) and crystallized therefrom yielding 3.5 g of N-(1,2,3,4-tetrahydronaphth-2-yl)-2-hydroxy-3-(4-indolyloxy)propanamine; m.p. 65°-68° C.

EXAMPLE 25

A mixture of 2-amino-6-hydroxytetralin (2.6 g) and 1-(2-allylphenoxy)- 2,3-epoxypropane (3.05 g) in absolute ethanol (80 ml) is refluxed for 5 hours. The solvent is removed by evaporation under reduced pressure and the residue is dissolved in a mixture isopropanol/ethyl ether 1/1 v/v. The solution is made acidic by the addition of HCl/isopropanol and the precipitate is recovered by filtration yielding 2.8 g of N-(6-hydroxy-1,2,3,4-tetrahydronaphth-2-yl)-2-hydroxy-3-(2-allylphenoxy)-propanamine hydrochloride; m.p. 212°-215° C.

EXAMPLE 26

A mixture of 2-amino-6-hydroxytetralin (0.9 g) and 1-(2-methylphenoxy)-2,3-epoxypropane (0.91 g) in absolute ethanol (30 ml) is refluxed for 5 hours. The solvent is evaporated off, the residue is dissolved in isopropanol (120 ml) and the obtained solution is made acidic by the addition of HCl/isopropanol. The precipitate which forms is recovered by filtration and crystallized from 95% ethanol giving 0.55 g of N-(6-hydroxy-1,2,3,4-tetrahydronaphth-2-yl)-2-hydroxy-3-(2-methylphenoxy)propanamine hydrochloride; m.p. 232°-234° C.

EXAMPLE 27

2-Aminotetralin (1.4 g) is added to a solution of 1-(2,3-epoxypropoxy)phenothiazine (2.71 g) in absolute ethanol (30 ml) and the obtained reaction mixture is refluxed for 8 hours. The solvent is then evaporated off under reduced pressure, the residue is dissolved in isopropanol, the obtained solution is heated and hydrogen chloride saturated isopropanol is stirred in. The precipitate is recovered by filtration affording N-(1,2,3,4-tetrahydronaphth-2-yl)-2-hydroxy-3-(1-phenothiazinyloxy)propanamine hydrochloride ((i): R=H, Ar=radical 2 wherein Z is >S, and the chain is attached to position 2 of the tetralin moiety).

EXAMPLE 28

Following the procedure of Example 27, but starting from 6-(2,3-epoxypropoxy)-1-oxo-1,2,3,4-tetrahydro-beta-carboline (2.46 g), N-(1,2,3,4-tetrahydronaphth-2-yl)-2-hydroxy-3-(1-oxo-1,2,3,4-tetrahydro-beta-carbolin-6-yloxy)propanamine hydrochloride is obtained ((i): R=H, Ar=radical 3 wherein Z is >C=O and Z' is H, and the chain is attached to position 2 of the tetralin moiety).

EXAMPLE 29

Operating as described in Example 27, but starting from a solution of 1-(2,3-epoxypropoxy)-9,10-dihydro-9,10-ethanoanthracene (2.78 g) in ethanol (30 ml), N-(1,2,3,4-tetrahydronaphth-2-yl)-2-hydroxy-3-(9,10-dihydro-9,10-ethanoanthr-1-yloxy)propanamine hydrochloride is obtained ((i): R=H, Ar=radical 5 wherein Z is ethylene, and the chain is attached to position 2 of the tetralin moiety).

EXAMPLE 30

Following the general procedure of Example 27, but starting from 5-(2,3-epoxypropoxy)coumarin (2.18 g) in ethanol (30 ml), N-(1,2,3,4-tetrahydronaphth-2-yl)-2-hydroxy-3-(coumarin-5-yloxy)propanamine hydrochloride is obtained ((i): R=H, Ar=radical 8 wherein Z is hydrogen, and the chain is attached to position 2 of the tetralin moiety).

EXAMPLE 31

A mixture of 2-aminotetralin (22.7 g), 3-chloro-2-hydroxy-1-(4-methylcoumarin-7-yloxy)propane (26.9 g), in absolute ethanol (35 ml) is charged in a sealed vessel and heated to 100° C. for 4 hours. The reaction mixture is then cooled and concentrated under reduced pressure. The residue is taken up in 1N hydrochloric acid (200 ml) and the aqueous solution is washed with chloroform and neutralized with sodium carbonate. Water is then evaporated off and the residue is taken up with isobutylmethylketone and filtered. Hydrogen chloride is then bubbled into the filtrate to precipitate N-(1,2,3,4-tetrahydronaphth-2-yl)-2-hydroxy-3-(4-methylcoumarin-7-yloxy)propanamine hydrochloride, ((i): R=H, Ar=radical 8 wherein Z is methyl, and the chain is attached to position 2 of the tetralin moiety) which is then crystallized from isopropanol.

EXAMPLE 32

A mixture of 5-hydroxy-3-methyl-1-phenylpyrazole (or 3-methyl-1-phenyl-1,2-pyrazolin-5-one) (5.22 g), epichlorohydrin (16.6 g) and piperidine (2 drops) is heated to 110° C. for 90 minutes and then concentrated under reduced pressure. The obtained residue is treated with 33% sodium hydroxide (45 ml) under stirring for 30 minutes, and then extracted with chloroform. The organic phase is washed with water, dried and concentrated under reduced pressure to afford a residue which is dissolved in chloroform and passed through a silica gel column. The obtained 5-(2,3-epoxypropoxy)-3-methyl-1-phenylpyrazole (2.5 g) is dissolved in absolute ethanol (30 ml) and 2-aminotetralin (1.61 g) is then added thereto. Following the general method described in Example 27, N-(1,2,3,4-tetrahydronaphth-2-yl)-2-hydroxy-3-(3-methyl-1-phenylpyrazol-5-yloxy)-propanamine dihydrochloride ((i): R=H, Ar=radical 9 wherein Z is methyl and Z' is phenyl, and the chain is attached to position 2 of the tetralin moiety) is obtained.

EXAMPLE 33

A mixture of 3-hydroxy-2-methyl-4-oxopyrane (12.6 g), sodium hydroxide (4 g), epichlorohydrin (9.25 g) and water (50 ml) is stirred at room temperature, under nitrogen atmosphere, for 3 hours; then it is extracted four times with chloroform (120 ml) and the organic extracts are combined, washed with water, dried and evaporated to dryness yielding 8.3 g of 3-(2,3-epoxypropoxy)-2-methyl-4-oxopyrane. A mixture of said product and 2-aminotetralin (7.3 g) in absolute ethanol (100 ml) is charged into a sealed vessel, heated to 80° C. for 5 hours, then cooled and evaporated under reduced pressure. The obtained residue is dissolved into ethyl acetate and a solution of fumaric acid in ethyl acetate is then added thereto. The precipitate which forms is recovered by filtration and crystallized from ethanol affording N-(1,2,3,4-tetrahydronaphth-2-yl)-2-hydroxy-3-(2-methyl-4-oxopyran-3-yloxy)propanamine hydrogenfumarate ((i): R=H, Ar=radical 10 wherein Z is methyl, and the chain is attached to position 2 of the tetralin moiety).

EXAMPLE 34

By operating according to Example 27, but starting from 5-(2,3-epoxypropoxy)-3,4-dihydrocarbostyril (2 g) and 2-aminotetralin (1.35 g) in ethanol (40 ml), N-(1,2,3,4-tetrahydronaphth-2-yl)-2-hydroxy-3-(3,4-dihydrocarbostyryl-5-oxy)propanamine hydrochloride ((i): R=H, Ar=radical 11 wherein Z is H and the chain bridges position 4 of the radical Ar to position 2 of the tetralin moiety) is obtained.

EXAMPLE 35

A mixture of 4-hydroxy-9-oxofluorene (10 g) and sodium hydroxide (1.9 g) in water (100 ml) is refluxed under nitrogen atmosphere for 1 hour. The reaction mixture is then allowed to cool to 500° C., epichlorohydrin (7 g) is added thereto and the reaction mixture is then stirred at 50° C. for 16 hours. Acetone (40 ml) is added thereto and the obtained mixture is extracted three times with ethyl acetate. The organic extracts are combined, washed with water, dried over magnesium sulfate and evaporated to dryness under reduced pressure. The residue (13.5 g) is taken up in ethanol (150 ml) and 2-aminotetralin (8 g) is then added thereto. The reaction mixture is refluxed for 8 hours and then worked-up as described in Example 27, giving N-(1,2,3,4-tetrahydronaphth-2-yl)-2-hydroxy-3-(9-oxo-fluoren-4-yloxy)propanamine hydrochloride ((i): R=H, Ar=radical 13 wherein Z is >C=O, and the chain is attached to position 2 of the tetralin moiety).

EXAMPLE 36

Following the procedure described in Example 27, but starting from 2,3-dimethyl-4-(2,3-epoxypropoxy)indole (10 g) and 2-aminotetralin (6.9 g) in ethanol (100 ml), N-(1,2,3,4-tetrahydronaphth-2-yl)-2-hydroxy-3-(2,3-dimethylindol-4-yloxy)propanamine hydrochloride is obtained ((i): R=H, Ar=radical 14 wherein Z is methyl, and the chain is attached to position 2 of the tetralin moiety).

EXAMPLE 37

Following the procedure described in Example 27, but starting from ethyl 4-(2,3-epoxypropoxy)indole-2-carboxylate (25.1 g), obtained from ethyl 4-hydroxyindole-2-carboxylate and epichlorohydrin according to the method of Belgian Patent 739,545, and 2-aminotetralin (14.8 g) in ethanol (120 ml), N-(1,2,3,4-tetrahydronaphth-2-yl)-2-hydroxy-3-(2-ethoxycarbonylindol-4-yloxy)propanamine hydrochloride is obtained ((i): R=H, Ar=radical 15 wherein Z is ethoxy, and the chain is attached to position 2 of the tetralin moiety) which is crystallized from a mixture ethanol/isopropanol 2/1.

EXAMPLE 38

Following the procedure described in Example 27, but starting from ethyl 4-(2,3-epoxypropoxy)indole-2-acetate (27.5 g), obtained from ethyl 4-hydroxyindole-2-acetate and epichlorohydrin according to the method of Swiss Patent 526,542, and 2-aminotetralin (14.8 g) in ethanol (120 ml), N-(1,2,3,4-tetrahydronaphth-2-yl)-2-hydroxy-3-(2-ethoxycarbonylmethylindol-4-yloxy)-propanamine hydrochloride is obtained ((i): R=H, Ar=radical 16 wherein Z is ethoxy, and the chain is attached to position 2 of the tetralin moiety) which is crystallized from a mixture ethanol/isopropanol 2/1.

EXAMPLE 39

Following the procedure described in Example 27, but starting from 2-ethyl-4-(2,3-epoxypropoxy)indole (10 g), obtained from 2-ethyl-4-hydroxyindole and epichlorohydrin according to the method described in Swiss Patent 527,188, and 2-aminotetralin (7.95 g) in ethanol (90 ml), N-(1,2,3,4-tetrahydronaphth-2-yl)-2-hydroxy-3-(2-ethylindol-4-yloxy)propanamine hydrochloride is obtained ((i): R=H, Ar=radical 17 wherein Z is ethyl, and the chain is attached to position 2 of the tetralin moiety).

EXAMPLE 40

Following the procedure described in Example 27, but starting from 4-(2,3-epoxypropoxy)-2-oxoindoline (20.5 g) and 2-aminotetralin (14.81 g) in ethanol (150 ml), N-(1,2,3,4-tetrahydronaphth-2-yl)-2-hydroxy-3-(2-oxo-2,3-dihydroindol-4-yloxy)propanamine hydrochloride is obtained, ((i): R=H, Ar=radical 18 wherein Z is H, and the chain is attached to position 2 of the tetralin moiety).

EXAMPLE 41

Following the general method described in Example 27, but starting from 8-(2,3-epoxypropoxy)thiochromane (22.2 g), obtained from 8-hydroxythiochromane and epichlorohydrin according to the teaching of Belgian Patent 765,313, and 2-aminotetralin (14.82 g), N-(1,2,3,4-tetrahydronaphth-2-yl)-2-hydroxy-3-(thiochroman-8-yloxy)propanamine hydrochloride is obtained ((i): R=H, Ar=radical 19 wherein Z is H and the chain bridges position 8 of the Ar radical and position 2 of the tetralin moiety).

EXAMPLE 42

Following the procedure described in Example 27, but starting from 7-(2,3-epoxypropoxy)-3-methylindene (19 g), obtained from 3-methyl-7-indenol and epichlorohydrin according to the teaching of JP 73-01070, and 2-aminotetralin (14.83 g), N-(1,2,3,4-tetrahydronaphth-2-yl)-2-hydroxy-3-(3-methylinden-7-yloxy)propanamine hydrochloride is obtained ((i): R=H, Ar=radical 23 wherein Z is H et Z' is methyl, and the chain is attached to position 2 of the tetralin moiety).

EXAMPLE 43

Following the procedure described in Example 27, but starting from 2-acetyl-7-(2,3-epoxypropoxy)benzofuran (23.2 g), obtained from 2-acetyl-7- hydroxybenzofuran and epichlorohydrin according to the teaching of Belgian Patent 783,440, and 2-aminotetralin (14.81 g) in ethanol (120 ml), N-(1,2,3,4-tetrahydronaphth-2-yl)-2-hydroxy-3-(2-acetylbenzofuran-7-yloxy)propanamine hydrochloride is obtained ((i): R=H, Ar=radical 24 wherein Z is acetyl and the chain bridges position 4 of the Ar group to position 2 of the tetralin moiety).

EXAMPLE 44

By operating as described in Example 43, but starting from 2-acetyl-4-(2,3-epoxypropoxy)benzofuran, N-(1,2,3,4-tetrahydronaphth-2-yl)-2-hydroxy-3-(2-acetylbenzofuran-4-yloxy)propanamine hydrochloride is obtained ((iF), L''=H, E'' and G'', together, form a group —CH=C(COCH$_3$)—O—, R is H, and the chain is attached to position 2 of the tetralin moiety).

EXAMPLE 45

Following the procedure of Example 27, but starting from 4-(4,5,6,7-tetrahydrobenzofuran-2-yl)-1-(2,3-epoxypropoxy)benzene (27 g), obtained according to the teaching of U.S. Pat. No. 3,894,058, and 2-aminotetralin (14.85 g) in ethanol (150 ml), N-(1,2,3,4-tetrahydronaphth-2-yl)-2-hydroxy-3-[[4-(4,5,6,7-tetrahydrobenzofuran-2-yl)]phenoxy]propanamine hydrochloride is obtained ((i): R=H, Ar=radical 31 wherein Z is H, and the chain is attached to position 2 of the tetralin moiety).

EXAMPLE 46

Following the procedure of Example 27, but starting from 4-(2,3-epoxypropoxy)-2,1,3-benzothiadiazole (20.8 g), prepared according to the teaching of DE-2,404,858, and 2-aminotetralin (14.82 g) in absolute ethanol (125 ml), N-(1,2,3,4-tetrahydronaphth-2-yl)-2-hydroxy-3-(2,1,3-benzothiadiazol-4-yloxy)propanamine hydrochloride is obtained ((i): R=H, Ar=radical 32, and the chain is attached to position 2 of the tetralin moiety).

EXAMPLE 47

Following the procedure described in Example 27, but starting from 7-(2,3-epoxypropoxy)phtalide (20.6 g), obtained from 7-hydroxyphtalide and epichlorohydrin according to the teaching of Belgian Patent 815,745, and 2-aminotetralin (14.81 g) in absolute ethanol (125 ml), N-(1,2,3,4-tetrahydronaphth-2-yl)-2-hydroxy-3-phtalid-7-yloxypropanamine hydrochloride is obtained ((iF): L''=H, E'' and G'' taken together, form a group —CO—O—CH$_2$—, R=H, and the chain is attached to position 2 of the tetralin moiety).

EXAMPLE 48

By operating as described in Example 27, but starting from khellin quinol 2,3-epoxypropyl ether (28.8 g) and 2-aminotetralin (14.83 g) in absolute ethanol (150 ml), the hydrochloride of khellin quinol 3-(1,2,3,4-tetrahydronaphth-2-ylamino)-2-hydroxypropyl ether is obtained ((i): R=H, Ar=radical 34, and the chain is attached to position 2 of the tetralin moiety).

EXAMPLE 49

Following the procedure of Example 27, but starting from 4-(2,3-epoxypropoxy)-1-oxoindane (18.8 g, see JP 49-048649) and 2-aminotetralin (14.81 g) in absolute ethanol (120 ml), N-(1,2,3,4-tetrahydronaphth-2-yl)-2-hydroxy-3-(1-oxoindan-4-yloxy)propanamine hydrochloride is obtained ((i): R=H, Ar=radical 35, and the chain is attached to position 2 of the tetralin moiety).

EXAMPLE 50

Following the procedure of Example 27, but starting from 4-(2,3-epoxypropoxy)-2-oxoindoline (20.3 g, see JP 49-094666) and 2-aminotetralin (14.81 g) in ethanol (100 ml), N-(1,2,3,4-tetrahydronaphth-2-yl)-2-hydroxy-3-(2-oxoindolin-4-yloxy)-propanamine hydrochloride is obtained ((i): R=H, Ar=radical 36, and the chain is attached to position 2 of the tetralin moiety).

EXAMPLE 51

Following the procedure of Example 35, but starting from 1-hydroxy-9-oxofluorene, N-(1,2,3,4-tetrahydronaphth-2-yl)-2-hydroxy-3-(9-oxofluoren-1-yloxy)-propanamine hydrochloride is obtained ((i): R=H, Ar=radical 37, and the chain is attached to position 2 of the tetralin moiety).

EXAMPLE 52

A mixture of 4-hydroxy-2-methoxymethylindole (8.3 g), epichlorohydrin (8.9 g) and sodium hydroxide (1.92 g) in water (35 ml) and dioxane (35 ml) is stirred at room temperature for 24 hours, and then it is extracted with methylene chloride. The organic phase is dried and evaporated to dryness. The obtained residue (10.2 g) is taken up in absolute ethanol (80 ml) and 2-aminotetralin (6.49 g) is added thereto. By operating then as described in Example 27, N-(1,2,3,4-tetrahydronaphth-2-yl)-2-hydroxy-3-(2-methoxymethylindol-4-yloxy)propanamine hydrochloride is obtained ((i): R=H, Ar=radical 38, and the chain is attached to position 2 of the tetralin moiety).

EXAMPLE 53

Following the procedure of Example 27, but starting from 2,2,5,7,8-pentamethyl-6-(2,3-epoxypropoxy)chromane (27.4 g), prepared by the method described in NL-A-6911816, and 2-aminotetralin (14.85 g), N-

(1,2,3,4-tetrahydronaphth-2-yl)-2-hydroxy-3-(2,2,5,7,8-pentamethylchroman-6-yloxy)propanamine hydrochloride is obtained ((i): R=H, Ar=radical 41, and the chain is attached to position 2 of the tetralin moiety).

EXAMPLE 54

Following the procedure of Example 27, but starting from 5-(2,3-epoxypropoxy)-1-oxotetralin (20.2 g), prepared as described in BE 739,195, and 2-aminotetralin (14.81 g) in absolute ethanol (130 ml), N-(1,2,3,4-tetrahydronaphth-2-yl)-2-hydroxy-3-(1-oxo-1,2,3,4-tetrahydronaphth-5-yloxy)propanamine hydrochloride is obtained ((iA), R=H, E and G, taken together form a group —$CH_2$—$CH_2$—$CH_2$—CO—, and the chain is attached to position 2 of the tetralin moiety).

EXAMPLE 55

Following the procedure of Example 27, but starting from 7-(2,3-epoxypropoxy)indene (18.8 g), obtained from 7-hydroxyindene and epichlorohydrin by the method described in DE 1,955,229, and 2-aminotetralin (14.85 g) in absolute ethanol (120 ml), N-(1,2,3,4-tetrahydronaphth-2-yl)-2-hydroxy-3-inden-7-yloxypropanamine hydrochloride is obtained ((i): R=H, Ar=radical 43, and the chain is attached to position 2 of the tetralin moiety).

EXAMPLE 56

Following the procedure of Example 27, but starting from 8-(2,3-epoxypropoxy)-2H-chromene (20.4 g) and 2-aminotetralin (14.85 g) in absolute ethanol (120 ml), N-(1,2,3,4-tetrahydronaphth-2-yl)-2-hydroxy-3-(2H-chromen-8-yloxy)-propanamine hydrochloride is obtained ((i): R=H, Ar=radical 44, and the chain is attached to position 2 of the tetralin moiety).

EXAMPLE 57

A mixture of 1,4-dihydroxyindane (1.4 g), epichlorohydrin (1 g) and sodium hydroxide (0.4 g) is water (15 ml) is stirred at room temperature for 24 hours and then it is extracted with ethyl ether. The organic phase is dried and evaporated to dryness and the obtained residue (1.2 g) is taken up in absolute ethanol (20 ml). A solution of 2-aminotetralin (0.87 g) in ethanol (10 ml) is added thereto and the reaction mixture is then processed as decribed in Example 27. N-(1,2,3,4-tetrahydronaphth-2-yl)-2-hydroxy-3-(1-hydroxyindan-4-yloxy)propanamine hydrochloride is thus obtained ((i): R=H, Ar=radical 45, and the chain is attached to position 2 of the tetralin moiety).

EXAMPLE 58

Following the procedure of Example 27, but starting from 4-(2,3-epoxypropoxy)indane (19 g) and 2-aminotetralin (14.81 g) in absolute ethanol (150 ml), N-(1,2,3,4-tetrahydronaphth-2-yl)-2-hydroxy-3-indan-4-yloxypropanamine hydrochloride is obtained ((iA): E and G, taken together, represent a group —$CH_2$—$CH_2$—$CH_2$—, R=H, and the chain is attached to position 2 of the tetralin moiety).

EXAMPLE 59

Following the general procedure of Example 27, but starting from 4-(2,3-epoxypropoxy)-1,2-benzisothiazole (20.7 g) prepared as described in BE 863,622, and 2-aminotetralin (14.82 g) is absolute ethanol (150 ml), N-(1,2,3,4-tetrahydronaphth-2-yl)-2-hydroxy-3-(1,2-benzisothiazol- 4-yloxy)propanamine hydrochloride is obtained ((i): R=H, Ar=radical 58, and the chain is attached to position 2 of the tetralin moiety).

EXAMPLE 60

Following the procedure of Example 27, but starting from 4-(2,3-epoxypropoxy)-3-methyl-1,2-benzisoxazole (20.5 g) (DE-2,711,382) and 2-aminotetralin (14.82 g) in absolute ethanol (150 ml), N-(1,2,3,4-tetrahydronaphth-2-yl)-2-hydroxy-3-(3-methyl-1,2-benzisoxazol-4-yloxy)propanamine hydrochloride is obtained ( (i), R=H, Ar=radical 59, and the chain is attached to position 2 of the tetralin moiety).

EXAMPLE 61

A solution of sodium hydroxide (1.175 g) in water (16 m) is added to a solution of 4-hydroxy-2-benzimidazolinone (4 g) in methanol (24 ml) and epichlorohydrin (4.16 g) is then added to the obtained mixture. After stirring at room temperature for 17 hours, the solvent is evaporated off and the residue is extracted with ethyl acetate. The organic extract is washed with water, dried over magnesium sulfate and concentrated to dryness. The residue is taken up in ethanol (30 ml) and a solution of 2-aminotetralin (4.35 g) in ethanol (20 ml) is then added thereto. The reaction mixture is then processed as described in Example 27 affording N-(1,2,3,4-tetrahydronaphth-2-yl)- 2-hydroxy-3-(2-oxobenzimidazolin-4-yloxy)propanamine hydrochloride ((i): R=H, Ar=-radical 61, Z=Z'=H, and the chain is attached to position 2 of the tetralin moiety).

EXAMPLE 62

Following the procedure of Example 27, but starting from 3-(2,3-epoxypropoxy)-2-cyanothiophene (18.1 g), prepared by the method described in DE-2,720,613 and 2-aminotetralin (14.8 g) in ethanol (100 ml), N-(1,2,3,4-tetrahydronaphth-2-yl)-2-hydroxy-3-(2-cyanothien-3-yloxy)propanamine hydrochloride is obtained ((i): R=H, Ar=radical 62 wherein Z is H, the cyano group is at position 2 of the Ar radical and the chain bridges position 5 of the Ar group to position 2 of the tetralin moiety).

EXAMPLE 63

Following the procedure of Example 27, but starting from 4-(4-ethoxycarbonyl-1,2,3-thiadiazol-5-yl)-1-(2,3-epoxypropoxy)benzene (2.94 g) and 2-aminotetralin (1.49 g) in absolute ethanol (20 ml), N-(1,2,3,4-tetrahydronaphth-2-yl)-2-hydroxy-3-[4-(4-ethoxycarbonyl-1,2,3-thiadiazol-5-yl)phenoxy]propanamine hydrochloride is obtained ((i): R=H, Ar=radical 63, wherein Z is a 4-$COOC_2H_5$ group, and the chain is attached to position 2 of the tetralin moiety).

EXAMPLE 64

Following the procedure of Example 27, but starting from 2-[3-(2,3-epoxypropoxy)phenyl]-4-trifluoromethylimidazole (2.81 g), prepared as described in DE-2,608,448 and 2-aminotetralin (1.5 g) in absolute ethanol (20 ml), N-(1,2,3,4-tetrahydronaphth-2-yl)-2-hydroxy-3-[3-(4-trifluoromethylimidazol-2-yl)phenoxy]propanamine hydrochloride is obtained ((i): R=H, Ar=radical 64, wherein Z is trifluoromethyl, the positions of attachment of the imidazole to the benzene ring are 2 and 4 respectively and the chain is attached to position 2 of the tetralin moiety).

EXAMPLE 65

A solution of sodium (2.3 g) in methanol (40 ml) is added to a solution of 3-pyridinol (9.5 g) in dimethylsulfoxide (100 ml). Methanol is then evaporated off under reduced pressure and epichlorohydrin (10.2 g) is added to the resulting solution kept at 25° C. The reaction mixture is stirred at 25° C. for 4 hours then poured into ice/water (500 ml) and extracted with chloroform (100 ml+75 ml+50 ml+25 ml). The organic extracts are pooled, washed with water (50 ml), dried and evaporated to afford 3-(2,3-epoxypropoxy)pyridine as an oily residue. Part of said oily product (3 g) is dissolved in ethanol (20 ml) and a solution of 2-aminotetralin (3 g) in ethanol (20 ml) is added thereto. Following then the procedure of Example 27, N-(1,2,3,4-tetrahydronaphth-2-yl)-2-hydroxy-3-pyrid-3-yloxypropanamine hydrochloride is obtained ((i): R=H, Ar=radical 65, wherein Z is H, and the chain is attached to position 2 of the tetralin moiety).

EXAMPLE 66

Following the procedure of Example 27, but starting from 1-acetyl-5-(2,3-epoxypropoxy)-1,2,3,4-tetrahydroquinoline (2.77 g) and 2-aminotetralin (1.49 g) in ethanol (30 ml), N-(1,2,3,4-tetrahydronaphth-2-yl)-2-hydroxy-3-(1-acetyl-1,2,3,4-tetrahydroquinolin-5-yloxy)propanamine hydrochloride is obtained ((i): R=H, Ar=radical 66, wherein Z is methyl, and the chain is attached to position 2 of the tetralin moiety).

EXAMPLE 67

Following the procedure of Example 27, but starting from 1-acetyl-4-(2,3-epoxypropoxy)indazole (2.33 g) prepared as described in BE 853,949, and 2-aminotetralin (1.49 g) in ethanol (30 ml), N-(1,2,3,4-tetrahydronaphth-2-yl)-2-hydroxy-3-(1-acetylindazol-4-yl)propanamine hydrochloride ((i): R=H, Ar=radical 67, wherein Z is H, Z' is acetyl, and the chain is attached to position 2 of the tetralin moiety).

EXAMPLE 68

Following the procedure of Example 27, but starting from 4-(2,3-epoxypropoxy)indazole (1.91 g), prepared as described in BE 853,949, and 2-aminotetralin (1.49 g) in absolute ethanol (30 ml), N-(1,2,3,4-tetrahydronaphth-2-yl)-2-hydroxy-3-indazol-4-ylpropanamine hydrochloride is obtained ((i): R=H, Ar=radical 67, wherein Z= Z'=H, and the chain is attached to position 2 of the tetralin moiety).

EXAMPLE 69

Following the procedure of Example 27, but starting from 6-(2,3-epoxypropoxy)-1-hydroxyxanthen-9-one (2.84 g), prepared as described in U.S. Pat. No. 3,912,733, and 2-aminotetralin (1.49 g) in absolute ethanol (40 ml), N-(1,2,3,4-tetrahydronaphth-2-yl)-2-hydroxy-3-(1-hydroxy-9-oxoxanth-6-yloxy)propanamine hydrochloride is obtained ((i): R=H, Ar=radical 1, wherein Z is H, and the chain is attached to position 2 of the tetralin moiety).

EXAMPLES 70 TO 77

Following the procedure of Example 32, and reacting epichlorohydrin with 4-hydroxy-2-methylbenzofuran, 4-hydroxybenzofuran, 5-hydroxybenzofuran, 5-hydroxy-2-methylbenzofuran, 6-hydroxy-3-methylbenzofuran or 7-hydroxybenzofuran, in the presence of piperidine, dissolving the thus obtained raw epoxide in absolute ethanol and adding thereto an ethanol solution of 2-aminotetralin, the following compounds are obtained respectively N-(1,2,3,4-tetrahydronaphth-2-yl)-2-hydroxy-3-(2-methylbenzofuran-4-yloxy)propanamine hydrochloride (Ex. 70);

N-(1,2,3,4-tetrahydronaphth-2-yl)-2-hydroxy-3-benzofuran-4-yloxypropanamine hydrochloride (Ex. 71);

N-(1,2,3,4-tetrahydronaphth-2-yl)-2-hydroxy-3-benzofuran-5-yloxypropanamine hydrochloride (Ex. 72);

N-(1,2,3,4-tetrahydronaphth-2-yl)-2-hydroxy-3-(2-methylbenzofuran-5-yloxy)propanamine hydrochloride (Ex. 73);

N-(1,2,3,4-tetrahydronaphth-2-yl)-2-hydroxy-3-(3-methylbenzofuran-6-yloxy)propanamine hydrochloride (Ex. 74); and N-(1,2,3,4-tetrahydronaphth-2-yl)-2-hydroxy-3-benzofuran-7-yloxypropanamine hydrochloride (Ex. 75), (i.e. compounds (i): R=H, Ar=radical 27, wherein one of Z and Z' is H and the other is methyl, and the chain is attached to position 2 of the tetralin moiety).

Analogously, starting from, respectively, 4-hydroxybenzothiophene or 5-hydroxybenzothiophene, the following compounds are obtained:

N-(1,2,3,4-tetrahydronaphth-2-yl)-2-hydroxy-3-benzothien-4-yloxypropanamine hydrochloride (Ex. 76); and N-(1,2,3,4-tetrahydronaphth-2-yl)-2-hydroxy-3-benzothien-5-yloxypropanamine hydrochloride (Ex. 77), ((i): R=H, Ar=radical 28, wherein Z is H, and the chain bridges position 4 or 5 of the Ar group to position 2 of the tetralin moiety).

EXAMPLE 78

Following the procedure of Example 33, but starting from 7-hydroxy-3-methylthiophene and epichlorohydrin in the presence of sodium hydroxide and contacting a solution of the obtained raw epoxide in absolute ethanol with a solution of 2-aminotetralin in absolute ethanol, N-(1,2,3,4-tetrahydronaphth-2-yl)-2-hydroxy-3-(3-methylbenzothien-7-yloxy)propanamine hydrochloride is obtained ((i): R=H, Ar=radical 28, wherein Z is methyl and the chain bridges position 7 of the Ar radical and position 2 of the tetralin moiety).

EXAMPLES 79 TO 81

Following the procedure of Example 32, but starting from 5-hydroxy-1,4-benzodioxane and epichlorohydrin in the presence of piperidine and reacting an ethanol solution of the obtained epoxide with an ethanol solution of 2-aminotetralin, N-(1,2,3,4-tetrahydronaphth-2-yl)-2-hydroxy-3-(1,4-benzodioxan-5-yloxy)propanamine hydrochloride (Ex. 79) is obtained ((iF): E" and G", taken together represent a group —O—CH$_2$—CH$_2$—O—, L" and R are hydrogen and the chain is attached to position 2 of the tetralin moiety).

Analogously, but starting from 6-hydroxy-3,4-dihydro-2H-1,5-benzodioxepine or 7-hydroxy-2,3,4,5-tetrahydro-1,6-benzodioxocine, the following compounds are obtained respectively:

N-(1,2,3,4-tetrahydronaphth-2-yl)-2-hydroxy-3-(3,4-dihydro-2H-1,5-benzodioxepin-6-yloxy)propanamine hydrochloride (Ex. 80); and N-(1,2,3,4-tetrahydronaphth-2-yl)-2-hydroxy-3-(2,3,4,5-tetrahydro-1,6-benzodioxocin-7-yloxy)propanamine hydrochloride (Ex. 81), ((i): R=H, Ar=radical 48, wherein n is 3 or 4 respectively, and the chain is attached to position 2 of the tetralin moiety).

EXAMPLES 82 AND 83

Following the procedure of Example 33, but starting from epichlorohydrin and 8-hydroxyquinoline or 5-hydroxyquinoline in the presence of sodium hydroxide and then treating an alcohol solution of the thus obtained epoxide with an alcohol solution of 2-aminotetralin, the following compounds are obtained respectively:
N-(1,2,3,4-tetrahydronaphth-2-yl)-2-hydroxy-3-quinolin-8-yloxypropanamine hydrochloride (Ex. 82) ((i): R=H, Ar=radical 50, and the chain is attached to position 2 of the tetralin moiety), and
N-(1,2,3,4-tetrahydronaphth-2-yl)-2-hydroxy-3-quinolin-5-yloxypropanamine hydrochloride (Ex. 82) ((i): R=H, Ar=radical 49, and the chain is attached to position 2 of the tetralin moiety).

EXAMPLE 84

Operating as described in Example 27, but starting from 8-acetylmethoxy-5-(2,3-epoxypropoxy)-3,4-dihydrocarbostyril, prepared by reacting 5,8-dihydroxy-3,4-dihydrocarbostyril with bromoacetone in the presence of potassium carbonate and in a mixture water/acetone 4/1, at the reflux temperature for 5 hours, and 2-aminotetralin (1.48 g) in absolute ethanol (30 ml), N-(1,2,3,4-tetrahydronaphth-2-yl)-2-hydroxy-3-(8-acetylmethoxy-3,4-dihydrocarbostyril-5-yloxy)propanamine hydrochloride is obtained ((iF): R=H, L"=acetonyloxy, E" and G", taken together, represent a group —$CH_2$—$CH_2$—CO—NH—, and the chain is attached to position 2 of the tetralin moiety).

EXAMPLES 85 A 88

Following the procedure of Example 27, but starting from 2-propargyloxy-1-(2,3-epoxypropoxy)benzene (2.04 g) and 2-aminotetralin in absolute ethanol (30 ml), N-(1,2,3,4-tetrahydronaphth-2-yl)-2-hydroxy-3-(2-propargyloxyphenyl)propanamine hydrochloride is obtained, m.p. 129°–130° C. (Ex. 85).

Analogously, starting from 2-propargyloxy-1-(2,3-epoxypropoxy)-benzene (2.04 g) and 1-aminotetralin (1.48 g), or 2-amino-7-hydroxytetralin (1.64 g), or 2-amino-6-hydroxytetralin (1.64 g), the following compounds are obtained, respectively:
N-(1,2,3,4-tetrahydronaphth-1-yl)-2-hydroxy-3-(2-propargyloxyphenyl)propanamine hydrochloride, m.p. 114°–116° C. (Ex. 86);
N-(7-hydroxy-1,2,3,4-tetrahydronaphth-2-yl)-2-hydroxy-3-(2-propargyloxyphenyl)propanamine hydrochloride, m.p. 158°–160° C. (Ex. 87); and
N-(6-hydroxy-1,2,3,4-tetrahydronaphth-2-yl)-2-hydroxy-3-(2-propargyloxyphenyl)propanamine hydrochloride, m.p. 179°–182° C. (Ex. 88).

EXAMPLES 89 AND 90

Following the procedure of Example 27, but starting from 1-(2-acetamido-3-nitrophenoxy)-2,3-epoxypropane (5 g) and 2-aminotetralin (2.96 g) in absolute ethanol (80 ml), N-(1,2,3,4-tetrahydronaphth-2-yl)-2-hydroxy-3-(2-acetamido-3-nitrophenoxy)propanamine hydrochloride is obtained ((iA): R=H, E=acetamido, G=nitro, and the chain is attached to position 2 of the tetralin moiety) (Ex. 89). A mixture of N-(1,2,3,4-tetrahydronaphth-2-yl)-2-hydroxy-3-(2-acetamido-3-nitrophenoxy)propanamine hydrochloride (4 g) and 97% formic acid (19 ml) is charged in a hydrogenation vessel and freezed. The air contained in the reaction vessel is replaced by nitrogen and 10% Pd/C (0.25 g) is rapidly introduced therein. Hydrogenation is carried out at room temperature and 2.5 bar until the theoretical amount of hydrogen has been consumed. The reaction mixture is then heated, at atmospheric pressure, for 2 hours by means of a boiling water-bath. The catalyst is filtered off, the filtrate is evaporated to dryness and the obtained residue is taken up in hydrogen chloride saturated-isopropanol.

N-(1,2,3,4-tetrahydronaphth-2-yl)-2-hydroxy-3-benzimidazol-4-yloxypropanamine dihydrochloride is thus obtained ((iF): R=L"=H, E" G", taken together, form a group —N=CH—NH—, and the chain is attached to position 2 of the tetralin moiety) (Ex. 90).

EXAMPLES 91 AND 92

A mixture of 4-hydroxy-9-oxoxanthene (1.1 g), epichlorohydrin (4 g) and piperidine (0.01 g) is heated on a boiling water-bath for 5 hours. Excess epichlorohydrin is then removed by distillation and the residue is dissolved in ethyl acetate (50 ml). The organic solution is washed with 2N NaOH (20 ml) and concentrated to dryness yielding 1-chloro-2-hydroxy-3-(9-oxoxanth-4-yloxy)propane (0.6 g) as a raw product. A solution of this product in absolute ethanol (20 ml) is then added to a solution of 2-aminotetralin (0.3 g) in ethanol (10 ml) and the mixture is refluxed for 4 hours and then evaporated to dryness. The obtained residue is taken up in hydrogen chloride saturated-isopropanol affording the desired N-(1,2,3,4-tetrahydronaphth-2-yl)-2-hydroxy-3-oxoxanth-4-yloxypropanamine hydrochloride ((i): R=H, Ar=radical 29, wherein Z is >C=O, and the chain is attached to position 2 of the tetralin moiety)(Ex. 91). Analogously, but starting from 4-hydroxyxanthene, N-(1,2,3,4-tetrahydronaphth-2-yl)-2-hydroxy-3-xanth-4-yloxypropanamine hydrochloride is obtained ((i): R=H, Ar=radical 29, wherein Z is a methylene group, and the chain is attached to position 2 of the tetralin moiety) (Ex. 92).

EXAMPLES 93 TO 96

Following the procedure of Example 91, but starting from 4-hydroxy-1-methylcarbostyril, 4-hydroxy-1-ethylcarbostyril, 4-hydroxy-1-allylcarbostyril, or 4-hydroxy-1-phenylcarbostyril and reacting the raw chlorohydrin thus obtained with 2-aminotetralin, the following compounds are prepared respectively:
N-(1,2,3,4-tetrahydronaphth-2-yl)-2-hydroxy-3-(1-methyl-2-oxo-1,2-dihydroquinolin-4-yloxy)propanamine hydrochloride (Ex. 93);
N-(1,2,3,4-tetrahydronaphth-2-yl)-2-hydroxy-3-(1-ethyl-2-oxo-1,2-dihydroquinolin-4-yloxy)propanamine hydrochloride (Ex. 94);
N-(1,2,3,4-tetrahydronaphth-2-yl)-2-hydroxy-3-(1-allyl-2-oxo-1,2-dihydroquinolin-4-yloxy)propanamine hydrochloride (Ex. 95); and
N-(1,2,3,4-tetrahydronaphth-2-yl)-2-hydroxy-3-(1-phenyl-2-oxo-1,2-dihydroquinolin-4-yloxy)propanamine hydrochloride (Ex. 96);
((i): R=H, Ar=radical 30, wherein Z is methyl, ethyl, allyl and phenyl respectively; and the chain is attached to position 2 of the tetralin moiety).

EXAMPLE 97

Following the procedure of Example 27, but starting from 1-(1-phenyltetrazol-5-yloxy)-2,3-epoxypropane (4.37 g) prepared as described in BE 866,278 and 2- aminotetralin (1.48 g) in absolute ethanol (60 ml), N-(1,2,3,4-tetrahydronaphth-2-yl)-2-hydroxy-3-(1-phenyltetrazol-5-yloxy)propanamine hydrochloride is obtained ((i): R=H, Ar=radical 60, wherein Z=Z'=H and the chain is attached to position 2 of the tetralin moiety).

EXAMPLE 98

A mixture of 1-(2-naphthyloxy)-2,3-epoxypropane (1.95 g), 2-aminotetralin (2.65 g) and ethanol (35 ml) is heated to the reflux temperature for 5 hours. The solvent is then evaporated off and the thus obtained solid residue is crystallized from ethyl acetate (5 ml), recovered by filtration, washed with ethyl acetate and then with ethyl ether, and dried yielding 1.8 g of N-(1,2,3,4-tetrahydronaphth-2-yl)-2-hydroxy-3-(2-naphthyloxy)-propanamine, as the free base; m.p. 102°–115° C.

EXAMPLE 99

Following the general procedure of Example 98, but starting from 1-(2-naphthyloxy)-2,3-epoxypropane (4.5 g) and 1-aminotetralin (2.95 g), N-(1,2,3,4-tetrahydronaphth-1-yl)-2-hydroxy-3-(2-naphthyloxy)propanamine free base is obtained as an oily product which is dissolved in an isopropyl ether/isopropanol 1/1 mixture (40 ml) and acidified with HCl/isopropanol. The corresponding hydrochloride is thus obtained which is crystallized from isopropanol (20 ml). Yield: 2.2 g; m.p. 135°–137° C.

EXAMPLE 100

Following the general procedure of Example 98, but starting from (R)-1-(1-naphthyloxy)-2,3-epoxypropane (3.8 g; /alpha/=−31.08° (c=1.5 % in methanol)), prepared from 1-naphthol by the method described in Heterocycles, 1983, 20, 1975–1978, and S(+)-1-aminotetralin (2.8 g) obtained from S(−)-1-aminotetralin hydrochloride (Il Farmaco Ed. Sci., 1971, 26, 475–486) by neutralization with 15% sodium hydroxide and extraction with ethyl ether, in the presence of S(−)-1-aminotetralin hydrochloride (5 mg), N-[(S)-1,2,3,4-tetrahydronaphth-1-yl]-(R)-2-hydroxy-3-(1-naphthyloxy)-propanamine is obtained as a yellow oil. Upon the addition of a small amount of isopropyl ether, the desired product crystallizes out and is recrystallized from isopropanol (50 ml) yielding 3.6 g; m.p. 107°–109° C., /alpha/= +6.6° (c=1% in methanol).

EXAMPLE 101

Following the general procedure of Examples 98 and 100, but starting from (S)-1-(1-naphthyloxy)-2,3-epoxypropane (4.5 g, /alpha/= +30.4° (c=1.5% in methanol), see Example 100) and R(−)-1-aminotetralin (3.3 g) obtained from the hydrochloride (Il Farmaco Ed. Sci., 1971, 26, 475–486), N-L[(R)-1,2,3,4-tetrahydronaphth-1-yl)](S) -D-2-hydroxy-3-(1-naphthyloxy)propanamine is obtained; m.p. 107°–109° C., /alpha/ = −6.5° (c=1%, methanol).

EXAMPLE 102

Starting from (R)-1-(1-naphthyloxy)-2,3-epoxypropane (4.5 g) and R(−)-1-aminotetralin (3.3 g), and following the general procedure of Example 99, but crystallizing the product from ethanol (50 ml) instead of isopropanol, N-](R)-1,2,3,4-tetrahydronaphth-1-yl)]-(R)-2-hydroxy-3-(1-naphthyloxy)propanamine hydrochloride (4.4 g) is obtained; m.p. 176°–178° C., /alpha/= +21.9° (c=1% in methanol).

EXAMPLE 103

Starting from (S)-1-(1-naphthyloxy)-2,3-epoxypropane (3.3 g), S(+)-1-aminotetralin (2.5 g) and a small amount of S(−)-1-aminotetralin hydrochloride (5 mg), and following the procedure of Example 102, N-[(S)-1,2,3,4-tetrahydronaphth-1-yl)]-(S)-2-hydroxy-3-(1-naphthyloxy)propanamine hydrochloride (3.4 g) is obtained; m.p. 177°–179° C., /alpha/ = −20.5° (c=1% in methanol).

EXAMPLES 104–107

The following compounds are obtained either as the free bases or the hydrochlorides, by operating as described in Examples 98 or 99:

N-(1,2,3,4-tetrahydronaphth-2-yl)-2-hydroxy-3-(5,6,7,8-tetrahydronaphth-1-yloxy)propanamine; m.p. 90°–93° C. (from ethyl acetate) (Ex. 104);

N-(7-hydroxy-1,2,3,4-tetrahydronaphth-2-yl)-2-hydroxy-3-naphth-2-yloxypropanamine hydrochloride; m.p. 184°–187° C. (from ethanol) (Ex. 105);

N-(7-hydroxy-1,2,3,4-tetrahydronaphth-2-yl)-2-hydroxy-3-(5,6,7,8-tetrahydronaphth-1-yloxy)-propanamine hydrochloride; m.p. 172°–175° C. (from isopropanol) (Ex. 106);

N-(1,2,3,4-tetrahydronaphth-1-yl)-2-hydroxy-3-(5,6,7,8-tetrahydronaphth-1-yloxy)propanamine hydrochloride; m.p. 172°–176° C. (from isopropanol) (Ex. 107).

EXAMPLES 108–112

By operating as described in Examples 98 or 99 the following compounds (iA) are obtained:

N-(1,2,3,4-tetrahydronaphth-1-yl)-2-hydroxy-3-(2-cyanophenoxy)-propanamine hydrochloride; m.p. 161°–163° C. (from isopropanol) (Ex. 108);

N-(1,2,3,4-tetrahydronaphth-1-yl)-2-hydroxy-3-(3-cyanophenoxy)-propanamine hydrochloride; m.p. 185°–187° C. (from 95% ethanol) (Ex. 109);

N-(1,2,3,4-tetrahydronaphth-1-yl)-2-hydroxy-3-(3-trifluoromethylphenoxy)propanamine hydrochloride; m.p. 135°–137° C. (from isopropanol) (Ex. 110);

N-(1,2,3,4-tetrahydronaphth-2-yl)-2-hydroxy-3-(3-trifluoromethylphenoxy)propanamine; m.p. 84°–89° C. (from isopropyl ether) (Ex. 111);

N-(7-hydroxy-1,2,3,4-tetrahydronaphth-2-yl)-2-hydroxy-3-(3-trifluoromethylphenoxy)propanamine hydrochloride; m.p. 215°–217° C. (from isopropanol) (Ex. 112).

EXAMPLES 113–119

The following compounds of formula (iB) are obtained by operating as described in Examples 98 or 99:

N-(1,2,3,4-tetrahydronaphth-1-yl)-2-hydroxy-3-(4-cyanophenoxy)propanamine hydrochloride; m.p. 156°–160° C. (from acetone) (Ex. 113);

N-(7-hydroxy-1,2,3,4-tetrahydronaphth-2-yl)-2-hydroxy-3-[4-(2-methoxyethyl)phenoxy]propanamine hydrochloride; m.p. 153°–156° C. (from isopropanol) (Ex. 114);

N-(1,2,3,4-tetrahydronaphth-2-yl)-2-hydroxy-3-[4-(2-methoxyethyl)phenoxy]propanamine; m.p. 95°–97° C. (from isopropyl ether) (Ex. 115);

N-(1,2,3,4-tetrahydronaphth-1-yl)-2-hydroxy-3-[4-(2-methoxyethyl)phenoxy]propanamine hydrochloride; m.p. 136°–139° C. (from isopropanol) (Ex. 116);

N-(7-hydroxy-1,2,3,4-tetrahydronaphth-2-yl)-2-hydroxy-3-(4-chlorophenoxy)propanamine hydrochloride; m.p. 168°–170° C. (from isopropanol) (Ex. 117);

N-1,2,3,4-tetrahydronaphth-2-yl)-2-hydroxy-3-(4-chlorophenoxy)-propanamine; m.p. 117°–119° C. (from ethyl acetate) (Ex. 118);

N-(1,2,3,4-tetrahydronaphth-1-yl)-2-hydroxy-3-(4-chlorophenoxy)propanamine hydrochloride; m.p. 131°–135° C. (from isopropanol) (Ex. 119).

EXAMPLES 120–122

Following the general procedure of Example 1, but starting from 1-aminotetralin, 2-aminotetralin or 2-amino-7-hydroxytetralin and 3-(2,3-epoxy-1-propoxy)-4-morpholino-1,2,5-thiadiazole, prepared as described in J. Org. Chem. 1979, 44, p. 1826, the following compounds are obtained respectively:

N-(1,2,3,4-tetrahydronapht-1-yl)-2-hydroxy-3-(4-morpholino-1,2,5-thiadiazol-4-yloxy)propanamine hydrochloride; m.p. 156°–159° C. (from isopropanol) (Ex. 120);

N-(1,2,3,4-tetrahydronapht-2-yl)-2-hydroxy-3-(4-morpholino-1,2,5-thiadiazol-4-yloxy)propanamine hydrochloride; p.f. 171°–174° C. (from isopropanol) (Ex. 121);

N-(7-hydroxy-1,2,3,4-tetrahydronapht-2-yl)-2-hydroxy-3-(4-morpholino-1,2,5-thiadiazol-4-yloxy)propanamine (as the free base avoiding the addition of HCl/isopropanol); p.f. 187°–191° C. (from isopropanol) (Ex. 122.).

EXAMPLE 123

(a) Epichlorohydrin (46.9 ml) is added to a solution of 3-chloro phenol (51.42 g) and sodium hydroxide (17.2 g) in water (70 ml) and the obtained reaction mixture is stirred at room temperature overnight and then extracted with ethyl ether. The organic phase is washed with 1N NaOH, and with water, dried over sodium sulfate, and concentrated to dryness under reduced pressure yielding 1-(3-chlorophenoxy)-2,3,-epoxypropane (46 g); b.p. 105°–110° C./0.5 mmHg.

(b) A mixture of the above product (2.77 g) and 1-aminotetralin (2.2 g) in absolute ethanol (75 ml) is refluxed for 5 hours, concentrated to dryness and applied to a silica gel column developed with ethyl acetate/cyclohexane 9/1 v/v. The combined fractions are concentrated to dryness, the obtained residue is dissolved in isopropanol (25 ml) and the solution is acidified by the addition of HCl/isopropanol. The precipitate is recovered by filtration yielding 1.6 g of N-(1,2,3,4-tetrahydronaphth-1-yl)-2-hydroxy-3-(3-chlorophenoxy)-propanamine hydrochloride; m.p. 157°–158° C.

EXAMPLE 124

A solution of 2-amino-7-hydroxytetralin (2.0 g) and 1-(3-chlorophenoxy)-2,3-epoxypropane (2.25 g) in absolute ethanol (50 ml) is heated to the reflux temperature for 5 hours. Ethanol is then evaporated off under reduced pressure and the obtained residue is chromatographed on a silica gel column eluting first with ethyl acetate and then with a mixture ethyl acetate/methanol 9/1 v/v up to complete elution of the product-containing fractions. The thus obtained fractions are pooled and evaporated to dryness. The residue is dissolved in isopropanol (20 ml) and the solution is acidified by the addition of HCl/isopropanol. A precipitate forms which is recovered by filtration and washed with ethyl ether yielding 2.2 g of N-(7-hydroxy-1,2,3,4-tetrahydronaphth-2-yl)-2-hydroxy-3-(3-chlorophenoxy)-propanamine hydrochloride; m.p. 193°–195° C.

EXAMPLE 125

A solution of 2-aminotetralin (1.1 g) and 1-(3-chlorophenoxy)-2,3-epoxypropane (1.38 g) in absolute ethanol (50 ml) is heated to the reflux temperature for 5 hours. Ethanol is evaporated off under reduced pressure and the residue is taken up in ethyl acetate (15 ml) and crystallized therefrom. The obtained product is then dissolved in isopropanol (20 ml) and the solution is made acidic by the addition of HCl/isopropanol. The precipitate which forms is recovered by filtration, and crystallized from 95% ethanol yielding 1.0 g of N-(1,2,3,4-tetrahydronaphth-2-yl)-2-hydroxy-3-(3-chlorophenoxy)-propanamine hydrochloride; m.p. 172°–174° C.

EXAMPLE 126

A solution of 1-aminotetralin (2.95 g) and [2-(2-propynyloxy)phenoxy]-2,3-epoxypropane (4.09 g) prepared by the method described in NL-A-6516433, in ethanol (100 ml) is heated to the reflux temperature for 5 hours. The solvent is then evaporated off and the obtained residue is chromatographed on a silica gel column eluting with ethyl acetate. Those fractions which contain the desired product are pooled and evaporated to dryness. The obtained residue is dissolved in isopropanol (25 ml) and the solution is made acidic by the addition of HCl/isopropanol. The precipitate which forms is recovered by filtration and crystallized from isopropanol (12 ml) yielding 2.25 g of N-(1,2,3,4-tetrahydronaphth-1-yl)-2-hydroxy-3-[2-(2-propynyloxy)phenoxy]propanamine hydrochloride; m.p. 114°–116° C.

EXAMPLE 127

Following the general procedure of Example 1, but starting from 2-amino-7-hydroxytetralin (2.55 g) and [2-(2-propynyloxy)phenoxy]-2,3-epoxypropane (3.18 g), a product is obtained which is washed with isopropanol first and then with ethyl ether yielding 2.6 g of N-(7-hydroxy-1,2,3,4-tetrahydronaphth-2-yl)-2-hydroxy-3-[2-(2-propynyloxy)phenoxy]propanamine hydrochloride; m.p. 158°–160° C.

EXAMPLE 128

Following the general procedure of Example 126, but starting from 2-aminotetralin instead of 1-aminotetralin, a precipitate is obtained which is washed with isopropanol first and then with ethyl ether yielding the desired N-(1,2,3,4-tetrahydronaphth-2-yl)-2-hydroxy-3-[2-(2-propynyloxy)phenoxy]propanamine hydrochloride; m.p. 129°–130° C.

EXAMPLE 129

Following the general procedure of Example 1, but starting from 2-amino-6-hydroxytetralin (0.6 g) and [2-(2-propynyloxy)-phenoxy]-2,3-epoxypropane (0.75 g), 0.2 g of N-(6-hydroxy-1,2,3,4-tetrahydronaphth-2-yl)-2-hydroxy-3-[2-(2-propynyloxy)phenoxy]propanamine hydrochloride is obtained; m.p. 179–°182° C.

EXAMPLE 130

A solution of 1-(2-chlorophenoxy)-2,3-epoxypropane (2.65 g) prepared by the method described in British Patent 767,991, and 2-aminotetralin (2.1 g) in ethanol (70 ml) is heated to the reflux temperature for 5 hours. Ethanol is then evaporated off and the thus obtained residue is chromatographed on a silica gel column eluting with ethyl acetate. The residue which is obtained upon evaporation to dryness of the combined fractions is crystallized from ethyl acetate (10 ml) yielding 1.5 g of N-(1,2,3,4-tetrahydronaphth-2-yl)-2-hydroxy-3-(2-chlorophenoxy)propanamine; m.p. 98°–101° C.

EXAMPLE 131

A mixture of 1-aminotetralin (2.95 g) and 1-(2-chlorophenoxy)-2,3-epoxypropane (3.69 g) in absolute ethanol (100 ml) is refluxed for 5 hours and then evaporated to dryness. The thus obtained residue is purified by silica gel column chromatography eluting with ethyl acetate/cyclohexane 7/3 v/v. The combined fractions are evaporated to dryness, the obtained residue is taken up in isopropanol (10 ml) and filtered. The solid on filter is crystallized from isopropanol (10 ml) and washed with hexane yielding 3.0 g of N-(1,2,3,4-tetrahydronaphth-1-yl)-2-hydroxy-3-(2-chlorophenoxy)propanamine; m.p. 78°–81° C.

EXAMPLE 132

A mixture of 2-amino-7-hydroxytetralin (1.9 g) and 1-(2-chlorophenoxy)-2,3-epoxypropane (2.15 g) in absolute ethanol (60 ml) is refluxed for 5 hours and then ethanol is evaporated off under reduced pressure. The thus obtained residue is chromatographed on a silica gel column eluting first with ethyl acetate up to the complete elution of the first spot and then with a mixture ethyl acetate/methanol 9/1 v/v. The obtained fractions are pooled and concentrated to dryness. The residue is dissolved in isopropanol (20 ml) and the obtained solution is acidified by the addition of HCl/isopropanol. The precipitate is recovered by filtration yielding 2.25 g of N-(7-hydroxy-1,2,3,4-tetrahydronaphth-2-yl)-2-hydroxy-3-(2-chlorophenoxy)propanamine hydrochloride; m.p. 201°–203° C.

EXAMPLE 133

A mixture of 2-aminotetralin (2.5 g) and 1-(4-acetamidophenoxy)-2,3-epoxypropane (3.52 g) in dimethylsulfoxide (40 ml) is heated at 80° C. for 5 hours. The reaction mixture is allowed to cool toat room temperature and water (180 ml) is then added thereto. The precipitate which forms is recovered by filtration and crystallized from absolute ethanol (120 ml) yielding 2.15 g of N-(1,2,3,4-tetrahydronaphth-2-yl)-2-hydroxy-3-(4-acetamidophenoxy)-propanamine; m.p. 133°–136° C.

EXAMPLE 134

A mixture of 1-aminotetralin (5.92 g) and 1-(4-acetamidophenoxy)-2,3-epoxypropane (8.30 g) in absolute ethanol (200 ml) is heated to the reflux temperature for 5 hours and then it is evaporated to dryness. The thus obtained residue is washed with isopropanol and then with ethyl ether, yielding 11.3 g of a product with m.p. 125°–130° C. Said product is dissolved in acidic water, the pH of the solution is brought to 10–11 by the addition of NaOH and the precipitate which forms is recovered by filtration, dissolved in a small amount of methanol, and purified by silica gel column chromatography eluting with ethyl acetate/methanol 9/1 v/v. The combined fractions are concentrated to dryness and washed with hexane yielding 2 g of N-(1,2,3,4-tetrahydronaphth1-yl)-2-hydroxy-3-(4-acetamidophenoxy)-propanamine; m.p. 80–°84° C.

EXAMPLE 135

A mixture of 1-aminotetralin (0.8 g) and 1-[(trans-6,7-dihydroxy-5,6,7,8-tetrahydronaphth-1-yl)oxy]-2,3-epoxypropane (1.3 g), prepared by the method described in J. Med. Chem., 1978, 21, No. 9, 913–922, in absolute ethanol (20 ml) is refluxed for 5 hours and the solvent is then evaporated off. The residue is chromatographed on a silica gel column eluting first with ethyl acetate and then with a mixture ethyl acetate/methanol 7/3 v/v. The combined fractions are evaporated to dryness yielding 1.0 g of N-(1,2,3,4-tetrahydronaphth-1-yl)-2-hydroxy-3-(trans-6,7-dihydroxy-5,6,7,8-tetrahydronaphth-1-yloxy)propanamine as a vitreous solid.

IR (KBr): 3362, 2930, 1454, 1253, 1065 cm-1.

EXAMPLE 136

(a) A solution of R(+)-2,3-epoxy-1-propanol (5 g), 2-allylphenol (7.54 g) and triphenylphosphine (14.7 g) in anhydrous tetrahydrofuran (80 ml) is cooled to 0°–5° C. and diethyl azodicarboxylate (11.7 g) is slowly dripped in. The reaction mixture is then allowed to stand at room temperature for 3 hours, the solvent is evaporated off and the thus obtained residue is taken up in ethyl ether and washed with 10% NaOH and then with water. The organic solution is dried over sodium sulfate and then concentrated under reduced pressure. The thus formed oily residue is chromatographed on a silica gel column eluting with a mixture hexane/ethyl acetate 7/3 v/v.

S(+)-1-(2-allylphenoxy)-2,3-epoxypropane (9.0 g) is thus obtained which is purified by distillation; b.p. 100°–105° C./0.3 mmHg, /alpha/=+14.3° (c=1% in methanol).

(b) A mixture of the above product (2.2 g) and S(−)-2-aminotetralin (1.7 g) in absolute ethanol (30 ml) is refluxed for 5 hours. Ethanol is then evaporated off and the obtained residue is purified by silica gel column chromatography eluting with ethyl acetate. The combined fractions are evaporated to dryness and the oily residue, taken up in a mixture ethyl acetate (10 ml)/hexane (10 ml), crystallizes therefrom.

N-[(S)-1,2,3,4-tetrahydronaphth-2-yl]-(S)-2-hydroxy-3-(2-allylphenoxy)propanamine (1.1 g) is then recovered by filtration and crystallized from isopropyl ether; m.p. 70°–72° C.; /alpha/=−51.0° (c=0.5% in methanol).

EXAMPLE 137

Following the general procedure of Example 136, but starting from R(+)-2-aminotetralin (2.2 g) and S(+)-1-(2-allylphenoxy)-2,3-epoxypropane (2.85 g), N-[-(R)-1,2,3,4-tetrahydronaphth-2-yl]-(S)-2-hydroxy-3-(2-allylphenoxy)propanamine (2.3 g) is obtained; m.p.. 65°–68° C.; /alpha/=+32.0° (c=0.5% in methanol).

EXAMPLE 138

(a) By operating as described in Example 136 (a), but using S(−)-2,3-epoxy-1-propanol instead of R(+)-2,3-epoxy-1-propanol, R(−)-1-(2-allylphenoxy)-2,3,-epoxypropane is obtained which is characterized by /alpha/=−11,8° C. (c=1% in methanol).

(b) A mixture of the above product (2.2 g) and S(−)-aminotetralin (1.7 g) in absolute ethanol (30 ml) is refluxed for 5 hours. Ethanol is then evaporated off and the obtained residue is purified by silica gel column chromatography eluting with ethyl acetate. Those fractions which contain the desired product are pooled together and concentrated to dryness. The residue is taken up in ethyl ether and filtered yielding 1.8 g of N-[(S)-1,2,3,4-tetrahydronaphth-2-yl-]-(R)-2-hydroxy-3-(2-allylphenoxy)-propanamine; m.p. 70°-72° C. (from ethyl acetate); /alpha/=−31.3° (c=0.5 % in methanol).

EXAMPLE 139

Starting from R(+)-2-aminotetralin (2.2 g) and R(−)-1-(2-allylphenoxy)-2,3-epoxypropane (2.85 g), and following the same procedure as in Example 138, 3.0 g of N-[(R)-1,2,3,4-tetrahydronaphth-2-yl]-(R)-2-hydroxy-3-(2-allylphenoxy)propanamine are obtained; m.p. 71-73° C. (from isopropyl ether); /alpha/=+53,6° (c=0,5% in methanol).

EXAMPLES 140-143

Following the general procedure of Examples 136-139, but using S(−)-2-amino-7-hydroxytetralin instead of S(−)-2-aminotetralin and R(+)-2-amino-7-hydroxytetralin instead of R(+)-2-aminotetralin, the compounds listed hereinbelow are obtained:

N-,[(S)-7-hydroxy-1,2,3,4-tetrahydronaphth-2-yl)]-(S)-2-hydroxy-3-(2-allylphenoxy)propanamine; m.p. 173°-174° C. (isopropyl ether); /alpha/=−79.6° (c=0.5% in methanol) (Ex. 140);

N-[(R)-7-hydroxy-1,2,3,4-tetrahydronaphth-2-yl)]-(S)-2-hydroxy-3-(2-allylphenoxy)propanamine; m.p. 167-°169° C. (isopropyl ether); /alpha/=+31.4° (c=0.5% in methanol) (Ex. 141);

N-[(S)-7-hydroxy-1,2,3,4-tetrahydronaphth-2-yl)]-(R)-2-hydroxy-3-(2-allylphenoxy)propanamine; m.p. 168-°170° C. (isopropyl ether); /alpha/=−36.3° (c=0.5% in methanol) (Ex. 142);

N-[-(R)-7-hydroxy-1,2,3,4-tetrahydronaphth-2-yl]-(R)-2-hydroxy-3-(2-allylphenoxy)propanamine; m.p. 173-°175° C. (isopropyl ether); alpha/=+75.6° (c=0.5% in methanol) (Ex. 143).

EXAMPLES 144-147

By operating substantially as described in Examples 136-139, but using S(−)-1-aminotetralin instead of S(−)-2-aminotetralin and R(+)-1-aminotetralin instead of R(+)-2-aminotetralin, the following compounds are obtained, either as the free base or as the hydrochlorides:

-N-[(S)-1,2,3,4-tetrahydronaphth-1-yl)]-(S)-2-hydroxy-3-(2-allylphenoxy)propanamine hydrochloride; m.p. 127°-129° C. (isopropanol); /alpha/=−23.4° (c 0.5 % in methanol) (Ex. 144);

N-[(R)-1,2,3,4-tetrahydronaphth-1-yl]-(S)-2-hydroxy-3-(2-allylphenoxy)propanamine; m.p. 71°-73° C. (isopropyl ether); /alpha/=−13.1° (c=0.5 % in methanol) (Ex. 145);

N-[(S)-1,2,3,4-tetrahydronaphth-1-yl)](R)-2-hydroxy-3-(2-allylphenoxy)propanamine; m.p. 72°-74° C. (isopropyl ether); /alpha/=+12.6° (c=0.5 % in methanol) (Ex. 146);

N-[(R)-1,2,3,4-tetrahydronaphth-1-yl)]-(R)-2-hydroxy-3-(2-allylphenoxy)propanamine hydrochloride; m.p. 126°-128° C. (isopropanol); alpha/=+21.7° (c=0.5 % in methanol) (Ex. 147).

We claim:

1. An aryloxypropanolaminotetralin compound of formula (i) and acid addition salts thereof

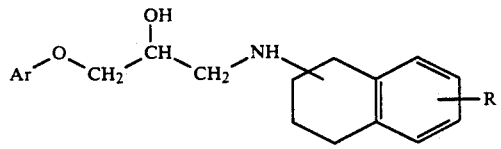

wherein R is hydrogen, hydroxy or methoxy; and
Ar represents naphthyl, tetralyl, indanyl, indenyl, phenyl or phenyl substituted by a group selected from the group consisting of halogen, cyano, hydroxy, amino, nitro, carboxyl, carbamoyl, trifluoromethyl, $C_{1-10}$alkyl, $C_{2-10}$alkenyl, $C_{2-10}$alkynyl, $C_{3-8}$cycloalkyl, $C_{1-7}$alkanoyl, $C_{1-10}$alkoxy, $C_{2-10}$hydroxyalkyl, $C_{2-10}$alkoxyalkyl, $C_{3-10}$alkoxyalkoxyalkyl, $C_{2-10}$alkoxyalkoxy, $C_{2-10}$alkenyloxy, $C_{3-10}$alkenyloxyalkyl, $C_{2-10}$alkynyloxy, $C_{3-10}$alkynyloxyalkyl, $C_{3-8}$cycloalkoxy, $C_{1-10}$alkylthio, $C_{2-10}$alkylthioalkyl, $C_{1-7}$acylamino, $C_{2-8}$acylaminoalkyl, $C_{1-6}$acyloxy, $C_{2-5}$alkoxycarbonyl, $C_{4-8}$cycloalkoxycarbonyl, and aminocarbonylamino.

2. A compound according to claim 1 wherein the acid addition salts are pharmaceutically acceptable.

3. A compound according to claim 1 of formula (iA) or (iB)

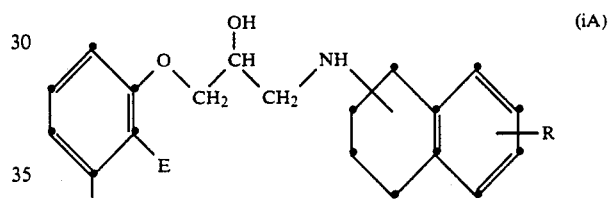

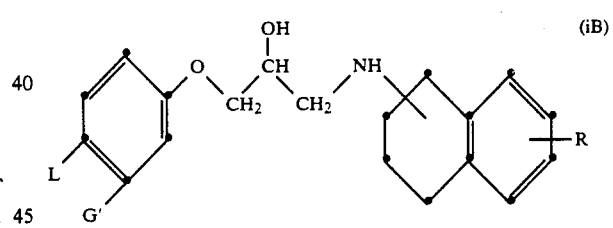

wherein R is hydrogen, hydroxy or methoxy;
E represents hydrogen, halogen, $C_{1-4}$alkyl, $C_{2-4}$alkenyl, $C_{2-4}$alkynyl, $C_{1-4}$alkoxy, $C_{2-4}$alkenyloxy, $C_{2-4}$alkynyloxy, $C_{3-6}$cycloalkyl, $C_{1-4}$alkylthio, $C_{1-4}$alkanoyl, or cyano;
G is hydrogen, halogen, $C_{1-10}$alkyl, $C_{2-10}$alkenyl, trifluoromethyl, or cyano, with the proviso that at least one of E and G is hydrogen;
G' is hydrogen;
L is halogen, $C_{1-4}$alkyl, $C_{1-4}$alkyl substituted with $C_{1-4}$alkoxy, $C_{2-4}$alkenyl, or cyano or E and G taken together can form a group —CH$_2$—CH$_2$—CH$_2$13, —CH$_2$—CH$_2$—CH$_2$—CH$_2$—, —CH=CH—CH$_2$—or —CH=CH—CH=CH—, and G' and L taken together can form a group —CH=CH—CH=CH.

4. A compound according to claim 3, of formula (iA) or (iB), wherein E is hydrogen, halogen, $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy and G is hydrogen; G' represents hydrogen and L is chloro, cyano or 2-methoxyethyl.

5. A compound according to claim 4, of formula (iA), wherein E is halogen, $C_{1-4}$alkyl, $C_{2-4}$alkenyl, $C_{1-4}$alkoxy, $C_{2-4}$alkenyoxy or $C_{2-4}$alkynyloxy.

6. A compound according to claim 3 which is N-(1,2,3,4-tetrahydronaphth-1-yl)-2-hydroxy-3-(1-naphthyloxy)-propanamine in optically active or inactive form and the pharmaceutically acceptable acid addition salts thereof.

7. A compound according to claim 6 which is N-[(R)-(1,2,3,4-tetrahydronaphth-1-yl)-2-hydroxy-3(1-naphthyloxy)-propanamine and the pharmaceutically acceptable acid addition salts thereof.

8. A compound according to claim 5 which is N-(7-hydroxy-1,2,3,4-tetrahydronaphth-2yl)-2-hydroxy-[3-(2-allylphenoxy)]propanamine in optically active or inactive form and the pharmaceutically acceptable acid addition salts thereof.

9. A compound according to claim 8 which is N-(7-hydroxy-1,2,3,4-tetrahydronaphth-2-yl)-2-hydroxy-[-3(2-allylphenoxy)]propanamine hydrochloride, in optically active or inactive form.

10. A pharmaceutical composition comprising an effective amount of a compound according to claim 2, as the active principle, wherein the active principle is admixed with a pharmaceutically acceptable carrier.

11. A pharmaceutical composition according to claim 10 in dosage unit form wherein the effective amount is from 0.1 to 500 mg of active principle.

* * * * *